US007235569B2

(12) United States Patent
Venkatesan et al.

(10) Patent No.: US 7,235,569 B2
(45) Date of Patent: Jun. 26, 2007

(54) PIPERIDINYL INDOLE AND TETROHYDROPYRIDINYL INDOLE DERIVATIVES AND METHOD OF THEIR USE

(75) Inventors: Aranapakam Mudumbai Venkatesan, Regopark, NY (US); Osvaldo Dos Santos, Kew Garden, NY (US); Yansong Gu, Pearl River, NY (US)

(73) Assignee: Wyeth, Madison, NJ (US)

( * ) Notice: Subject to any disclaimer, the term of this patent is extended or adjusted under 35 U.S.C. 154(b) by 54 days.

(21) Appl. No.: 10/835,998

(22) Filed: Apr. 30, 2004

(65) Prior Publication Data

US 2005/0004162 A1 Jan. 6, 2005

Related U.S. Application Data

(60) Provisional application No. 60/467,345, filed on May 2, 2003.

(51) Int. Cl.
*A61K 31/4439* (2006.01)
*A06K 31/443* (2006.01)
*C07D 401/14* (2006.01)
(52) U.S. Cl. .................. 514/339; 514/323; 546/201; 546/277.4
(58) Field of Classification Search ............... 546/201, 546/277.4; 514/323, 339
See application file for complete search history.

(56) References Cited

U.S. PATENT DOCUMENTS 5,693,655 A 12/1997 Bottcher et al. ............ 514/323

FOREIGN PATENT DOCUMENTS

| EP | 0 666 258 A1 | 8/1995 |
| WO | WO 99/67237 A1 | 12/1999 |
| WO | WO 00/34263 A1 | 6/2000 |
| WO | WO 00/43382 A1 | 7/2000 |

OTHER PUBLICATIONS

Arborelius, L. et al., "5-HT$_{1A}$ receptor antagonists increase the activity of serotonergic cells in the dorsal raphe nucleus in rats treated acutely or chronically with citalopram," *Naunyn-Schmiedeberg's Arch. Pharmacol.* 1995, 352: 157-165.
Invernizzi, R. et al., "Chronic treatment with citalopram facilitates the effect of a challenge dose on cortical serotonin output: role of presynaptic 5-HT$_{1A}$ receptors," *Eur. J. Pharmacol.* 1994, 260: 243-246.
Artigas, F. et al., "Acceleration of the effect of selected antidepressant drugs in major depression by 5-HT$_{1A}$ antagonists," *Trends Neurosci.* 1996, 19(9): 378-383.
Jean-Luc Malleron et al., "New Indole Derivatives as Potent and Selective Serotonin Uptake Inhibitors," *J. Med. Chem.* 1993, 36: 1194-1202 [plus erratum: p. 2242].

Wustrow et al., "3-[[(4-Aryl-1-piperazinyl)alkyl]cyclohexyl]-1H-indoles as Dopamine D2 Partial Agonists and Autoreceptor Agonists," *J. Med. Chem.* 1997, 40: 250-259.
Perez, V., et al., "Randomised double-blind, placebo-controlled trial of pindolol in combination with fluoxetine antidepressant treatment," *The Lancet*, 1997, 349: 1594-1597.
Feiger, A., "A Double-Blind Comparison of Gepirone Extended Release, Imipramine, and Placebo in the Treatment of Outpatient Major Depression," *Psychopharmacol. Bull.*, 1996, 32(4): 659-665.
Wilcox, C. et al., "A Double-Blind Trial of Low- and High-Dose Ranges of Gepirone-ER Compared With Placebo in the Treatment of Depressed Outpatients," *Psychopharmacol. Bull.*, 1996, 32(3): 335-342.
Grof, P. et al., "An open study of oral flesinoxan, a 5-HT$_{1A}$ receptor agonist, in treatment-resistant depression," *International Clinical Psychopharmacology*, 1993, 8: 167-172.
Dimitriou, E. et al., "Buspirone Augmentation of Antidepressant Therapy," *J. Clinical Psychopharmacol.*, 1998, 18(6): 465-469.
*Remington's Pharmaceutical Sciences*, 17th edition, ed. Alfonso R. Gennaro, Mack Publishing Company, Easton, Pa (1985).
Bundgaard (ed.), Design of Prodrugs, Elsevier (1985).
Higuchi and Stella (eds.), Prodrugs as Novel Drug Delivery Systems, American Chemical Society (1975).
Krogsgaard-Larsen, et al., (ed.), Design and Application of Prodrugs, Textbook of Drug Design and Development, Chapter 5, 113-191 (1991).
Bundgaard, H. et al., "Prodrugs as a means to improve the delivery of peptide drugs," *Advanced Drug Delivery Reviews*, Elsevier Science Publishers, 8:1-38 (1992).
Bundgaard, J. et al., "Glycolamide Esters as Biolabile Prodrugs of Carboxylic Acid Agents: Synthesis, Stability, Bioconversion, and Physicochemical Properties," *Pharmaceutical Sciences*, 77(4):285-298 (Apr. 1988).
Cheetham, S. C. et al., "[$^3$H]Paroxetine Binding in Rat Frontal Cortex Strongly Correlates With [$^3$H]5-HT Uptake: Effect of Administration of Various Antidepressant Treatments," *Neuropharmacol.*, 1993, 32: 737-743.
Cheng, Y-C. et al., "Relationship between the inhibition constant ($K_1$) and the concentration of inhibitor which causes 50 per cent inhibition ($I_{50}$) of an enzymatic reaction," *Biochem. Pharmacol.*, 1973, 22: 3099-3108.
Hall, M. D. et al. "[$^3$H]8-Hydroxy-2-(Di-n-Propylamino)Tetralin Binding to Pre- and Postsynaptic 5-Hydroxytryptamine Sites in Various Regions of the Rat Brain," *J. Neurochem.*, 1985, 44(6): 1685-1696.
Lazareno, S. and Birdsall, N.J.M., "Pharmacological characterization of acetylcholine-stimulated [$^{35}$S]-GTPγS binding mediated by human muscarinic m1—m4 receptors: antagonist studies," *Br. J. Pharmacol.*, 1993, 109:1120-1127.

*Primary Examiner*—Patricia L. Morris
(74) *Attorney, Agent, or Firm*—Woodcock Washburn LLP

(57) ABSTRACT

3-Piperidin-4-yl-1H-indole and 3-(1,2,3,6-tetrahydro-pyridin-4-yl)-1H-indole derivatives are disclosed. Methods of using the derivatives and compositions containing the derivatives in the prevention and/or treatment of serotonin disorders, such as depression and anxiety, are also disclosed. Additionally, processes for the preparation of 3-piperidin-4-yl-1H-indole and 3-(1,2,3,6-tetrahydro-pyridin-4-yl)-1H-indole derivatives are disclosed.

8 Claims, No Drawings

PIPERIDINYL INDOLE AND TETRAHYDROPYRIDINYL INDOLE DERIVATIVES AND METHOD OF THEIR USE

CROSS REFERENCE TO RELATED APPLICATIONS

The present application claims benefit of Provisional Application Ser. No. 60/467,345, filed May 2, 2003, the disclosure of which is hereby incorporated by reference in its entirety.

FIELD OF THE INVENTION

The present invention relates to 3-piperidin-4-yl-1H-indole and 3-(1,2,3,6-tetrahydro-pyridin-4-yl)-1H-indole derivatives, processes for preparing such derivatives, and the use of such derivatives to prevent and/or treat a variety of psychological disorders. Preferred compounds of this invention display activity both as 5-HT$_{1A}$ receptor antagonists and as serotonin uptake inhibitors, and are useful, inter alia, in the prevention and/or treatment of serotonin-related disorders.

BACKGROUND OF THE INVENTION

Major depressive disorder affects an estimated 340 million people worldwide. Depression is the most frequently diagnosed psychiatric disorder and, according to the World Health Organization, is the fourth greatest public health problem. If left untreated, the effects of depression can be devastating, robbing people of the energy or motivation to perform everyday activities and, in some cases, leading to suicide. Symptoms of the disorder include feelings of sadness or emptiness, lack of interest or pleasure in nearly all activities, and feelings of worthlessness or inappropriate guilt. In addition to the personal costs of depression, the disorder also has been estimated to result in more than $40 billion in annual costs in the United States alone, due to premature death, lost productivity, and absenteeism.

Pharmaceuticals that enhance serotonergic neurotransmission have had success in preventing and/or treating many psychiatric disorders, including depression and anxiety. The first generation of non-selective serotonin-affecting drugs operated through a variety of physiological functions that endowed them with several side-effect liabilities. A class of more recently-developed drugs, selective serotonin reuptake inhibitors (SSRIs), have had significant success in preventing and/or treating depression and related illnesses and have become among the most prescribed drugs since the 1980s. Although they have a favorable side effect profile compared to tricyclic antidepressants (TCAs), they have their own particular set of side effects due to the non-selective stimulation of serotonergic sites. They typically have a slow onset of action, often taking several weeks to produce their full therapeutic effect. Furthermore, they have generally been found to be effective in less than two-thirds of patients.

SSRIs are believed to work by blocking the neuronal reuptake of serotonin, increasing the concentration of serotonin in the synaptic space, thus increasing the activation of postsynaptic serotonin receptors. Although a single dose of an SSRI can inhibit the neuronal serotonin transporter, and thus would be expected to increase synaptic serotonin, long-term treatment is usually required before clinical improvement is achieved. It has been suggested that the delay in onset of antidepressant action of the SSRIs is the result of an increase in serotonin levels in the vicinity of the serotonergic cell bodies. This excess serotonin is believed to activate somatodendritic autoreceptors, i.e., 5-HT$_{1A}$ receptors, reduce cell firing activity, and, in turn, decrease serotonin release in major forebrain areas. This negative feedback limits the increment of synaptic serotonin that can be induced by antidepressants acutely. Over time, the somatodendritic autoreceptors become desensitized, allowing the full effect of the SSRIs to be expressed in the forebrain. This time period has been found to correspond to the latency for the onset of antidepressant activity. [Perez, et al., *The Lancet,* 1997, 349:1594–1597].

In contrast to the SSRIs, a 5-HT$_{1A}$ agonist or partial agonist acts directly on postsynaptic serotonin receptors to increase serotonergic neurotransmission during the latency period for the SSRI effect. Accordingly, the 5-HT$_{1A}$ partial agonist buspirone and gepirone [Feiger, A., *Psychopharmacol. Bull.,* 1996, 32: 659–665, Wilcox, C., *Psychopharmacol. Bull.,* 1996, 32: 335–342], and the 5-HT$_{1A}$ agonist flesinoxan [Grof, P., *International Clinical Psychopharmacology,* 1993, 8: 167–172], have shown efficacy in clinical trials for the treatment of depression. Furthermore, such agents are believed to stimulate the somatodendritic autoreceptors, thus hastening their desensitization and decreasing the SSRI latency period. Indeed, buspirone augmentation to standard SSRI therapy has been shown to produce marked clinical improvement in patients initially unresponsive to standard antidepressant therapy [Dimitriou, E., *J. Clinical Psychopharmacol.,* 1998, 18: 465–469].

There is still an unfulfilled need for a single agent with a dual mechanism of antidepressant action, i.e., one that not only inhibits or blocks serotonin reuptake (to increase levels of serotonin in the synapse) but also antagonizes the 5-HT$_{1A}$ receptors (to reduce the latency period). The present invention is directed to these, as well as other important ends.

SUMMARY OF THE INVENTION

This invention provides novel 3-piperidin-4-yl-1H-indole and 3-(1,2,3,6-tetrahydro-pyridin-4-yl)-1H-indole derivatives. In preferred embodiments, the compounds of this invention inhibit or block serotonin reuptake and/or are antagonists at the 5-HT$_{1A}$ receptor. The compounds of the invention are thus useful, inter alia, in the prevention and/or treatment of diseases affected by disorders of the serotonin-affected neurological systems, including, but not limited to, depression, anxiety, cognitive deficits, such as those resulting form Alzheimer's disease and other neurodegenerative disorders, schizophrenia, prostate cancer, and nicotine withdrawal.

In one aspect, the present invention provides 3-piperidin-4-yl-1H-indole and 3-(1,2,3,6-tetrahydro-pyridin-4-yl)-1H-indole derivatives having formula I:

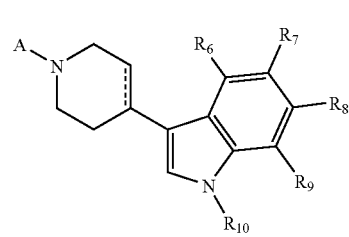

or a prodrug, N-oxide, stereoisomer or a pharmaceutically acceptable salt thereof; wherein:

A is a heterocycle selected having the following structure:

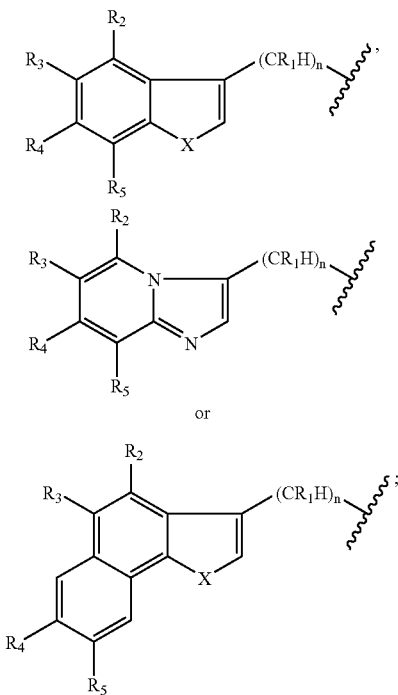

X is O or S;

$R_1$ is hydrogen, alkyl, cycloalkyl, alkenyl, alkynyl, fluoro, alkoxy, heteroaryloxy, cycloalkoxy, hydroxy, nitrile, carboxy, alkoxycarbonyl, alkylcarbonyl, aminocarbonylalkyl, alkylaminocarbonyl, fluorinated alkyl, aryl, aryloxy, alkylaryl, heteroaryl, alkylheteroaryl, $NH_2$, $NHR_{11}$, $NR_{11}R_{11}$, —O-alkyl-$NR_{11}R_{11}$, or -aryl-O-alkyl-$NR_{11}R_{11}$;

$R_2$, $R_3$, $R_4$, $R_5$, $R_6$, $R_7$, $R_8$ and $R_9$ are, independently, hydrogen, alkyl, cycloalkyl, alkenyl, alkynyl, halo, cyano, alkoxy, heteroaryloxy, cycloalkoxy, hydroxy, nitro, nitrile, $NH_2$, $NHR_{11}$, $NR_{11}R_{11}$, CHO, alkylcarbonyl, arylcarbonyl, carboxy, alkoxycarbonyl, alkoxycarbonylalkyl, alkylcarbonyloxy aminocarbonylalkyl, alkylaminocarbonyl, fluorinated alkyl, aryl, aryloxy, alkylaryl, heteroaryl, alkylheteroaryl, —O-alkyl-$NR_{11}R_{11}$, or -aryl-O-alkyl-$NR_{11}R_{11}$;

$R_{10}$ is hydrogen, alkyl, cycloalkyl, alkenyl of 3 to 6 carbon atoms (with the proviso that the carbon bearing the double bond should not be directly connected to N), alkynyl of 3 to 6 carbon atoms (with the proviso that the carbon bearing the triple bond should not be directly connected to N), alkoxycarbonyl, alkylcarbonyl, aminocarbonylalkyl, alkylaminocarbonyl, fluorinated alkyl, aryl, alkylaryl, heteroaryl, alkylheteroaryl, $SO_2$-aryl, or $SO_2$-alkyl;

$R_2$ and $R_3$, $R_3$ and $R_4$, or $R_4$ and $R_5$ can each be attached together to form a cycloalkyl or optionally substituted aromatic or hetero aromatic ring containing one or two hetero atoms such as N, O, S, S(=O) or $SO_2$;

$R_{11}$ is hydrogen, optionally substituted alkyl, optionally substituted alkenyl (with the proviso that the carbon bearing the double bond is not bonded directly to the heteroatoms such as O, S or N—$R_{11}$), optionally substituted alkynyl (with the proviso that the carbon bearing the triple bond is not bonded directly to the heteroatoms such as O, S or N—$R_{11}$), optionally substituted aryl, optionally substituted alkylaryl, heteroaryl optionally substituted with $R_2$, optionally substituted alkylheteroaryl, $SO_2$-aryl, $SO_2$-heteroaryl or $SO_2$-alkyl;

with the proviso that if two $R_{11}$, groups are attached to a nitrogen, then they can together form a 4- to 7-membered cyclic system having 0 to 2 hetero atoms selected from O, S=(O)$_r$, where r is an integer from 0 to 2, and $NR_{11}$; and n is an integer from 1 to 6.

In another aspect, the present invention is directed to compositions comprising a compound of formula I and one or more pharmaceutically acceptable carriers.

In another aspect, the present invention is directed to compositions comprising a compound of formula I, one or more pharmaceutically acceptable carriers, and an SSRI.

Also provided are methods for blocking or inhibiting the neuronal reuptake of serotonin and/or modulating the activity of 5-$HT_{1A}$ receptors through in vitro or in vivo administration of an effective amount of a compound of one or more compounds according to the invention. In this respect, such compounds preferably function as 5-$HT_{1A}$ antagonists.

The present invention also provides methods of preventing and/or treating a patient suspected of suffering from a serotonin-related disorder, comprising the step of administering to the patient a therapeutically effective amount of a compound of formula I.

In yet another aspect, the present invention is also directed to methods of inhibiting the reuptake of serotonin in a patient in need thereof, comprising the step of administering to the patient a therapeutically effective amount of a compound of formula I.

In other aspects, the present invention is also directed to methods of antagonizing 5-$HT_{1A}$ receptors in a patient in need thereof, comprising the step of administering to the patient a therapeutically effective amount of a compound of formula I.

In a further aspect, the present invention is directed to a method of antagonizing 5-$HT_{1A}$ receptors and inhibiting the reuptake of serotonin in a patient in need thereof, comprising the step of administering to the patient a therapeutically effective amount of a compound of formula I.

DETAILED DESCRIPTION OF THE INVENTION

The term "alkyl", as used herein, whether used alone or as part of another group, refers to a substituted or unsubstituted aliphatic hydrocarbon and includes, but is not limited to, straight and branched chains containing from 1 to 6 carbon atoms, unless explicitly stated otherwise. For example, methyl, ethyl, propyl, isopropyl, butyl, i-butyl and t-butyl are encompassed by the term "alkyl".

The term "optionally substituted alkyl", as used herein, refers to an aliphatic hydrocarbon and includes, but is not limited to, straight and branched chains containing from 1 to 6 carbon atoms, unless explicitly stated otherwise, optionally substituted with 1 or 2 substituents. Suitable substitutions for alkyl, include, but are not limited to, $R_2$ groups, as defined herein above, haloalkyl, haloalkoxy, cyano, alkylcarbonyl, alkoxycarbonylalkyl, and alkylcarbonyloxy.

The carbon number, as used in these definitions herein, refers to carbon backbone and carbon branching, but does not include carbon atoms of substituents, such as alkoxy substitutions and the like.

The term "alkenyl", as used herein, whether used alone or as part of another group, refers to an aliphatic hydrocarbon chain and includes, but is not limited to, straight and branched chains having 2 to 6 carbon atoms and containing at least one double bond.

The term "optionally substituted alkenyl", as used herein, refers to an aliphatic hydrocarbon and includes, but is not limited to, straight and branched chains containing from 3 to 6 carbon atoms and containing at least one double bond, optionally substituted with one or more $R_2$ groups, as defined herein above.

The term "alkynyl", as used herein, whether used alone or as part of another group, refers to an aliphatic hydrocarbon chain and includes, but is not limited to, straight and branched chains having 2 to 6 carbon atoms.

The term "optionally substituted alkynyl", as used herein, refers to an aliphatic hydrocarbon and includes, but is not limited to, straight and branched chains containing from 3 to 6 carbon atoms and containing at least one triple bond, optionally substituted with one or more $R_2$ groups, as defined herein above.

The term "cycloalkyl", as used herein, whether used alone or as part of another group, refers to a saturated or unsaturated, substituted or unsubstituted, alicyclic hydrocarbon group having 3 to 10 carbon atoms, including, but not limited to cyclopropyl, cyclobutyl, cyclopentyl, cyclohexyl or cycloheptyl. Specifically included within the definition of "cycloalkyl" are those alicylic hydrocarbon groups that are optionally substituted.

An optionally substituted cycloalkyl can be substituted with 1 or 2 substituents. Suitable substitutions for cycloalkyl include, but are not limited to, $R_2$ groups, haloalkyl, haloalkoxy, cyano, alkylcarbonyl, alkoxycarbonylalkyl, alkylcarbonyloxy and hetero atoms such as N, O, S, $NR_{11}$, or $S(O)_r$, where r is 0 to 2. For example, a cycloalkyl with substituted with 1 or 2 hetero atoms such as N—$R_{11}$, O, or $S(O)_r$, where r is 0 to 2, includes, but is not limited to, azetidine, pyrrolidine, morpholine, piperidine, piperazine, homopiperazine, tetrahydro, dihydrofuryl, tetrahydro, dihydro pyrane or thiopyran.

The term "aryl", as used herein, whether used alone or as part of another group, refers to a substituted or unsubstituted aromatic hydrocarbon ring group containing 6 to 10 carbon atoms, unless explicitly stated otherwise, and includes, but is not limited to phenyl, naphthalene, indene and indacene. Specifically included within the definition of "aryl" are those aromatic hydrocarbon chains that are optionally substituted. An optionally substituted aryl refers to a substituted or unsubstituted aromatic hydrocarbon ring group containing 6 to 10 carbon atoms, optionally substituted with 1 to 3 substitutents. Suitable substitutions for aryl, include, but are not limited to, $R_2$ groups, haloalkyl, haloalkoxy, cyano, alkylcarbonyl, alkoxycarbonylalkyl, and alkylcarbonyloxy.

The term "heteroaryl", as used herein, whether used alone or as part of another group, refers to a substituted or unsubstituted aromatic heterocycle ring system (moncyclic or bicyclic) of 4 to 10 carbon atoms, and contains from 1 to 3 heteroatoms selected from S, O or N. The term "heteroaryl" includes, but not limited to, furan, thiophene, pyrrole, imidazole, oxazole, thiazole, isoxazole, pyrazole, isothiazole, oxadiazole, triazole, thiadiazole, quinolizine, quinoline, isoquinoline, cinnoline, phthalazine, quinazoline, quinoxaline, napthyridine, pteridine, pyridine, pyrazine, pyrimidine, pyridazine, pyran, triazine, indole, isoindole, indazole, indolizine, and isobenzofuran. Specifically included with the definition of "heteroaryl" are those aromatic heterocyclic rings that are optionally substituted. An optionally substituted heteroaryl may be substituted with 1 to 3 substitutents, and more preferably 1 to 2 groups.

Suitable substitutions for heteroaryl, include, but are not limited to, $R_2$ groups, haloalkyl, haloalkoxy, cyano, alkylcarbonyl, alkoxycarbonylalkyl, and alkylcarbonyloxy.

The term "alkylaryl", as used herein, whether used alone or as part of another group, refers to the group —$R_a$—$R_b$—, containing 7 to 12 carbon atoms, wherein $R_a$ is an alkyl group, as defined above, $R_b$ is an aryl group, as defined above.

The term "optionally substituted alkylaryl" as used herein, refers to an alkylaryl group as defined above, optionally substituted with one or more $R_2$ groups.

The term "alkylheteroaryl", as used herein, whether used alone or as part of another group, refers to $R_a$—$R_a$, containing 7 to 12 carbon atoms, where $R_c$ is an alkyl group as defined above, and $R_c$ is a heteroaryl group, as defined above.

The term "optionally substituted alkylheteroaryl", as used herein, refers to an alkylheteroaryl group, as defined above, optionally substituted with one or more $R_2$ groups.

The term "amino", as used herein, refers to —$NH_2$, —$N(H)R_{11}$, or —$N(R_{11})R_{11}$.

The term "halo", as used herein, refers to means chloro, bromo, iodo or fluoro.

The term "alkoxy", as used herein, whether used alone or as part of another group, refers to a substituted or unsubstituted —O—$R_a$, where $R_a$ is an alkyl group containing 1 to 6 carbon atoms, as defined above. Specifically included within the definition of "alkoxy" are those alkoxy moieties that are optionally substituted. An optionally substituted alkoxy may be substituted with 1 or 2 $R_2$.

The term "alkoxyalkyl", as used herein, refers to the group —$R_a$—O—$R_a$, where $R_a$ is an alkyl group, as defined above.

The term "aryloxy", as used herein, whether used alone or as part of another group, refers to the group —O—$R_b$—, where $R_b$ is an aryl group, as defined above.

The term "—O-alkyl-$NR_{11}R_{11}$", as used herein, refers to the group —O—$R_a$—$N(R_{11})$—$R_{11}$ where $R_a$ is an alkyl group, as defined above.

The term "-aryl-O-alkyl-$NR_{11}R_{11}$", as used herein, refers to refers to the group $R_b$—O—$R_a$—$N(R_{11})$—$R_{11}$, where $R_a$ is an alkyl group and $R_b$ is an aryl group, as defined above.

The term "heteroaryloxy", as used herein, refers to the group $R_c$—O—, where $R_c$ is a heteroaryl group, as defined above.

The term "cycloalkoxy", as used herein, refers to a substituted or unsubstituted alicyclic alkoxy group having 3 to 6 carbon atoms. Specifically include with in the definition of "cycloalkoxy" are those alicyclic alkoxy groups that are optionally substituted. An optionally substituted cycloalkoxy may be substituted with 1 or more heteroatoms including, but not limited to O, S, and N—$R_{11}$.

The term "carbonylalkyl", as used herein, refers to the group —$R_a$—C(=O)—, where $R_a$ is an alkyl group containing 1 to 4 carbon atoms, as defined above.

The term "carbonylaryl", as used herein, refers to the group —$R_b$—C(=O), where $R_b$ is an aryl group, as defined above.

The term "alkoxycarbonyl", as used herein, refers to the group —O—$R_a$—C(=O)—, where $R_a$ is an alkyl group containing 1 to 4 carbon atoms, as defined above.

The term "alkoxycarbonylalkyl", as used herein, refers to the group —O—$R_a$—C(=O)—$R_a$—, where $R_a$ is an alkyl group containing 1 to 4 carbon atoms, as defined above.

The term "aminocarbonylalkyl", as used herein, refers to the group —$R_a$ C(=O)N($R_{11}$)($R_{11}$), where $R_a$ is an alkyl group containing 1 to 12 carbon atoms, as defined above.

The term "alkylaminocarbonyl", as used herein, refers to the group $(R_a)_2$—NH—C(=O), where $R_a$ is hydrogen or an alkyl group as defined above, containing 1 to 12 carbons.

The term "fluorinated alkyl", as used herein, refers to an alkyl group containing 1 to 4 carbon atoms, as defined above, substituted with 1 or more fluorine atoms.

The term "alkylcarbonyl", as used herein, refers to the group $R_a$—C(=O)—, where $R_a$ is an alkyl group containing 1 to 4 carbon atoms, as defined above.

The term "alkylcarbonyloxy", as used herein, refers to the group $R_a$—C(=O)O, where $R_a$ is an alkyl group containing 1 to 4 carbon atoms, as defined above.

The term "$SO_2$-aryl", as used herein, refers to the group $S(O_2)$—$R_b$, where $R_b$ is an aryl group, as defined above.

The term "$SO_2$-heteroaryl", as used herein, refers to the group $S(O_2)$—$R_b$, where $R_b$ is a heteroaryl group, as defined above.

The term "$SO_2$-alkyl", as used herein, refers to the group $S(O_2)$—$R_a$, where $R_a$ is an alkyl group, as defined above.

It is understood that the definition of the compounds of formula I, when $R_1$, $R_2$ or $R_3$, $R_4$ $R_5$, $R_6$, $R_7$, $R_8$ $R_9$, $R_{10}$ and $R_{11}$ contain asymmetric carbons, encompass all possible stereoisomers and mixtures thereof which possess the activity discussed below. In particular, it encompasses racemic modifications and any optical isomers which possess the indicated activity. Optical isomers may be obtained in pure form by standard separation techniques.

Preferred $R_1$ groups are hydrogen and alkyl. Particularly preferred are hydrogen, methyl, ethyl, propyl and isopropyl.

Preferred among the above noted $R_2$ to $R_9$ groups are hydrogen, halo, alkyl, alkoxy, alkenyl, $NR_{11}R_{11}$, and cyano. Particularly preferred are hydrogen, chloro, fluoro, methyl ethyl, propenyl, methoxy, and cyano.

Preferred $R_{10}$ groups are hydrogen, alkyl, aryl and heteroaryl. Particularly preferred are hydrogen and alkyl.

Preferred $R_{11}$, groups are hydrogen, alkyl, aryl and heteroaryl. Particularly preferred are hydrogen and alkyl.

Preferred aryl groups are phenyl and naphthalene.

Preferred heteroaryls include furan, thiophene, pyrrole, imidazole, oxazole, thiazole, isoxazole, pyrazole, isoxazole, isothiazole, oxadiazole, triazole, thiadiazole, quinolizine, quinoline, and isoquinoline. More preferred heteroaryls include furan, thiophene, imidazole, isoxazole, quinoline, pyridine and pyrazole.

The following compounds are particularly preferred:

3-{1-[2-(1-benzofuran-3-yl)ethyl]-1,2,3,6-tetrahydro-4-pyridinyl}-1H-indole;
3-{1-[2-(1-benzofuran-3-yl)ethyl]-1,2,3,6-tetrahydro-4-pyridinyl}-1-methyl-1H-indole;
3-{1-[2-(1-benzofuran-3-yl)ethyl]-1,2,3,6-tetrahydro-4-pyridinyl}-7-ethyl-1H-indole;
3-{1-[2-(1-benzofuran-3-yl)ethyl]-1,2,3,6-tetrahydro-4-pyridinyl}-6-fluoro-1H-indole;
3-{1-[2-(1-benzofuran-3-yl)ethyl]-1,2,3,6-tetrahydro-4-pyridinyl}-5-cyano-1H-indole;
3-{1-[2-(1-benzofuran-3-yl)ethyl]-1,2,3,6-tetrahydro-4-pyridinyl}-5-fluoro-1H-indole;
3-{1-[2-(6-chloro-1-benzofuran-3-yl)ethyl]-1,2,3,6-tetrahydro-4-pyridinyl}-1H-indole;
3-{1-[2-(6-chloro-1-benzofuran-3-yl)ethyl]-1,2,3,6-tetrahydro-4-pyridinyl}-5-fluoro-1H-indole;
3-{1-[2-(6-chloro-1-benzofuran-3-yl)ethyl]-1,2,3,6-tetrahydro-4-pyridinyl}-6-fluoro-1H-indole;
3-{1-[2-(6-methoxy-1-benzofuran-3-yl)ethyl]-1,2,3,6-tetrahydro-4-pyridinyl}-1H-indole;
3-{1-[2-(6-methoxy-1-benzofuran-3-yl)ethyl]-1,2,3,6-tetrahydro-4-pyridinyl}-5-fluoro-1H-indole;
3-{1-[2-(6-methoxy-1-benzofuran-3-yl)ethyl]-1,2,3,6-tetrahydro-4-pyridinyl}-6-fluoro-1H-indole;
3-{1-[2-(6-methoxy-1-benzofuran-3-yl)ethyl]-1,2,3,6-tetrahydro-4-pyridinyl}-6-cyano-1H-indole;
3-{1-[2-(5-chloro-1-benzofuran-3-yl)ethyl]-1,2,3,6-tetrahydro-4-pyridinyl}-1H-indole;
3-{1-[2-(5-chloro-1-benzofuran-3-yl)ethyl]-1,2,3,6-tetrahydro-4-pyridinyl}-5-fluoro-1H-indole;
3-{1-[2-(5-chloro-1-benzofuran-3-yl)ethyl]-1,2,3,6-tetrahydro-4-pyridinyl}-6-fluoro-1H-indole;
3-{1-[2-(5-fluoro-1-benzofuran-3-yl)ethyl]-1,2,3,6-tetrahydro-4-pyridinyl}-1H-indole;
3-{1-[2-(5-fluoro-1-benzofuran-3-yl)ethyl]-1,2,3,6-tetrahydro-4-pyridinyl}-5-cyano-1H-indole;
3-{1-[2-(5-fluoro-1-benzofuran-3-yl)ethyl]-1,2,3,6-tetrahydro-4-pyridinyl}-5-fluoro-1H-indole;
3-{1-[2-(7-methoxy-1-benzofuran-3-yl)ethyl]-1,2,3,6-tetrahydro-4-pyridinyl}-1H-indole;
3-{1-[2-(7-methoxy-1-benzofuran-3-yl)ethyl]-1,2,3,6-tetrahydro-4-pyridinyl}-6-fluoro-1H-indole;
3-{1-[2-(7-methoxy-1-benzofuran-3-yl)ethyl]-1,2,3,6-tetrahydro-4-pyridinyl}-5-fluoro-1H-indole;
3-{1-[2-(7-methoxy-1-benzofuran-3-yl)ethyl]-1,2,3,6-tetrahydro-4-pyridinyl}-5-cyano-1H-indole;
3-{1-[2-(5-methoxy-1-benzofuran-3-yl)ethyl]-1,2,3,6-tetrahydro-4-pyridinyl}-1H-indole;
3-{1-[2-(5-methoxy-1-benzofuran-3-yl)ethyl]-1,2,3,6-tetrahydro-4-pyridinyl}-5-fluoro-1H-indole;
3-{1-[2-(5-methoxy-1-benzofuran-3-yl)ethyl]-1,2,3,6-tetrahydro-4-pyridinyl}-6-fluoro-1H-indole;
3-{1-[2-(5-methoxy-1-benzofuran-3-yl)ethyl]-1,2,3,6-tetrahydro-4-pyridinyl}-7-ethyl-1H-indole;
3-{1-[2-(1-benzothiophene-3-yl)ethyl]-1,2,3,6-tetrahydro-4-pyridinyl}-1H-indole;
3-{1-[2-(1-benzothiophene-3-yl)ethyl]-1,2,3,6-tetrahydro-4-pyridinyl}-1-(2-propenyl)-1H-indole;
3-{1-[2-(1-benzothiophene-3-yl)ethyl]-1,2,3,6-tetrahydro-4-pyridinyl}-1-methyl-1H-indole;
3-{1-[2-(5-chloro-1-benzothiophene-3-yl)ethyl]-1,2,3,6-tetrahydro-4-pyridinyl}-1H-indole;
3-{1-[2-(5-chloro-1-benzothiophene-3-yl)ethyl]-1,2,3,6-tetrahydro-4-pyridinyl}-1-(2-propenyl)-1H-indole;
3-{1-[2-(5-chloro-1-benzothiophene-3-yl)ethyl]-1,2,3,6-tetrahydro-4-pyridinyl}-1-methyl-1H-indole;
3-{1-(2-naphtho[1,2-b]furan-3-yl-ethyl)-piperidin-4-yl]-1H-indole;
3-{1-[2-(1-benzofuran-3-yl)propyl]-1,2,3,6-tetrahydro-4-pyridinyl}-1H-indole;
3-{1-[2-(1-benzofuran-3-yl)propyl]-1,2,3,6-tetrahydro-4-pyridinyl}-6-fluoro-H-indole;
3-{1-[2-(1-benzofuran-3-yl)propyl]-1,2,3,6-tetrahydro-4-pyridinyl}-6-fluoro-1H-indole;
3-{1-[2-(7-methoxy-1-benzofuran-3-yl)propyl]-1,2,3,6-tetrahydro-4-pyridinyl}-1H-indole;
3-{1-[2-(7-methoxy-1-benzofuran-3-yl)propyl]-1,2,3,6-tetrahydro-4-pyridinyl}-5-fluoro-1H-indole;
3-{1-[2-(7-methoxy-1-benzofuran-3-yl)propyl]-1,2,3,6-tetrahydro-4-pyridinyl}-6-fluoro-1H-indole;
3-{1-[2-(7-methoxy-1-benzofuran-3-yl)-1-methylethyl]-1,2,3,6-tetrahydro-4-pyridinyl}-1H-indole;
3-{1-[2-(7-methoxy-1-benzofuran-3-yl)-1-methylethyl]-1,2,3,6-tetrahydro-4-pyridinyl}-6-fluoro-1H-indole;
3-{1-[2-(5-methoxy-1-benzofuran-3-yl)-1-methylethyl]-1,2,3,6-tetrahydro-4-pyridinyl}-1H-indole; and
3-{1-[2-(5-chloro-1-benzofuran-3-yl)ethyl]-1,2,3,6-tetrahydropyridin-4-yl}imidazo[1,2-a]pyridine.

The present invention provides a process for the preparation of a compound of general formula I. These compounds can be prepared by condensing the appropriately substituted 3-(1,2,3,6-tetrahydro-4-pyridinyl)1-H-indole derivatives 13 with the appropriately substituted heterocycles 15 to 17, as illustrated in Scheme 1, in polar aprotic solvents such as DMF, THF, DMSO, acetone or ethanol in the presence of an acid binding agent, such as an organic tertiary base, (such as triethylamine, triethanolamine, DBU, or diisopropylethylamine); or an alkailine metal carbonate such as potassium carbonate or sodium carbonate, at 100–150° C. The required appropriately substituted 3-(1,2,3,6-tetrahydro-4-pyridinyl)1-H-indole derivatives 13 can be prepared from the commercially available 4-piperidone monohydrate hydrochloride 14 and appropriately substituted indole, as illustrated in Scheme 2.

Scheme. 1

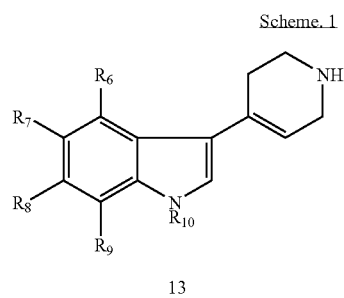

13

DMSO/ DIEA/
100° C.

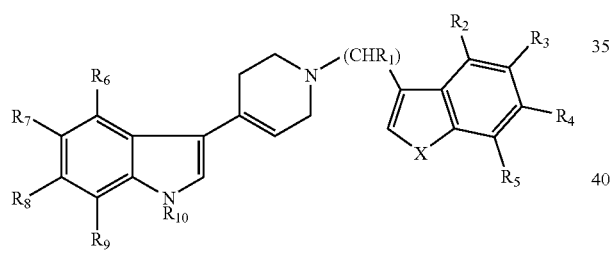

18 = X = O
19 = X = S

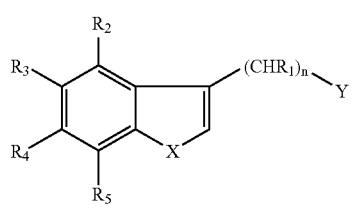

15 = X = O; Y = OTs or I
16 = X = S; Y = OTs or I

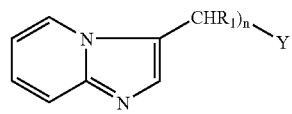

17 = Y = OTs or I

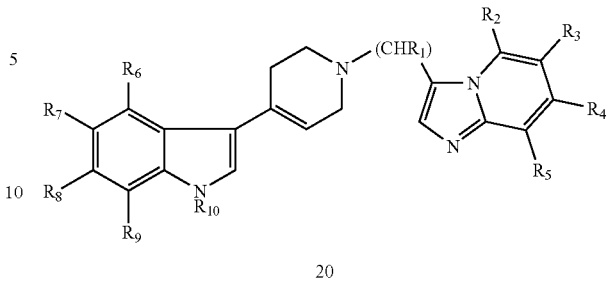

20

Scheme. 2

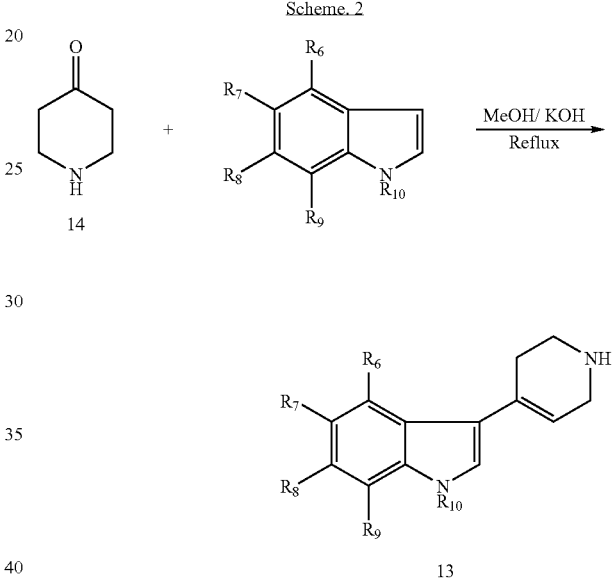

14

MeOH/ KOH
Reflux

13

The heterocycles 15 and 16 may be prepared from commercially available substituted salicyclic acid derivatives (Scheme 3). Appropriately substituted salicyclic derivatives or thiosalicyclic acid derivatives (Scheme 3) are esterified using alcoholic HCl. The compound 21 may be reacted with ethyl bromoacetate acid in refluxing acetone/$K_2CO_3$ The resultant diester 22 may be hydrolyzed to the diacid 23. The diacid obtained may be cyclized using anhydrous $CH_3COONa/(CH_3CO)_2O$ to produce compound 24. This may hydrolyzed using 1N HCl to produce compound 25. This compound, on reaction with (triphenylphosphoranylidene)ethylacetate or the appropriately substituted (triphenylphosphoranylidene)ethylacetate derivative, in boiling organic solvents such as toluene or xylenes, yields compound 26. This can be converted to 15 or 16 by reduction using LAH and converting it to either tosylate or iodide using $I_2$/imidazole. The reaction may be carried out in a temperature range of 80–120° C. at atmospheric pressure for 8–24 hours.

Scheme. 3
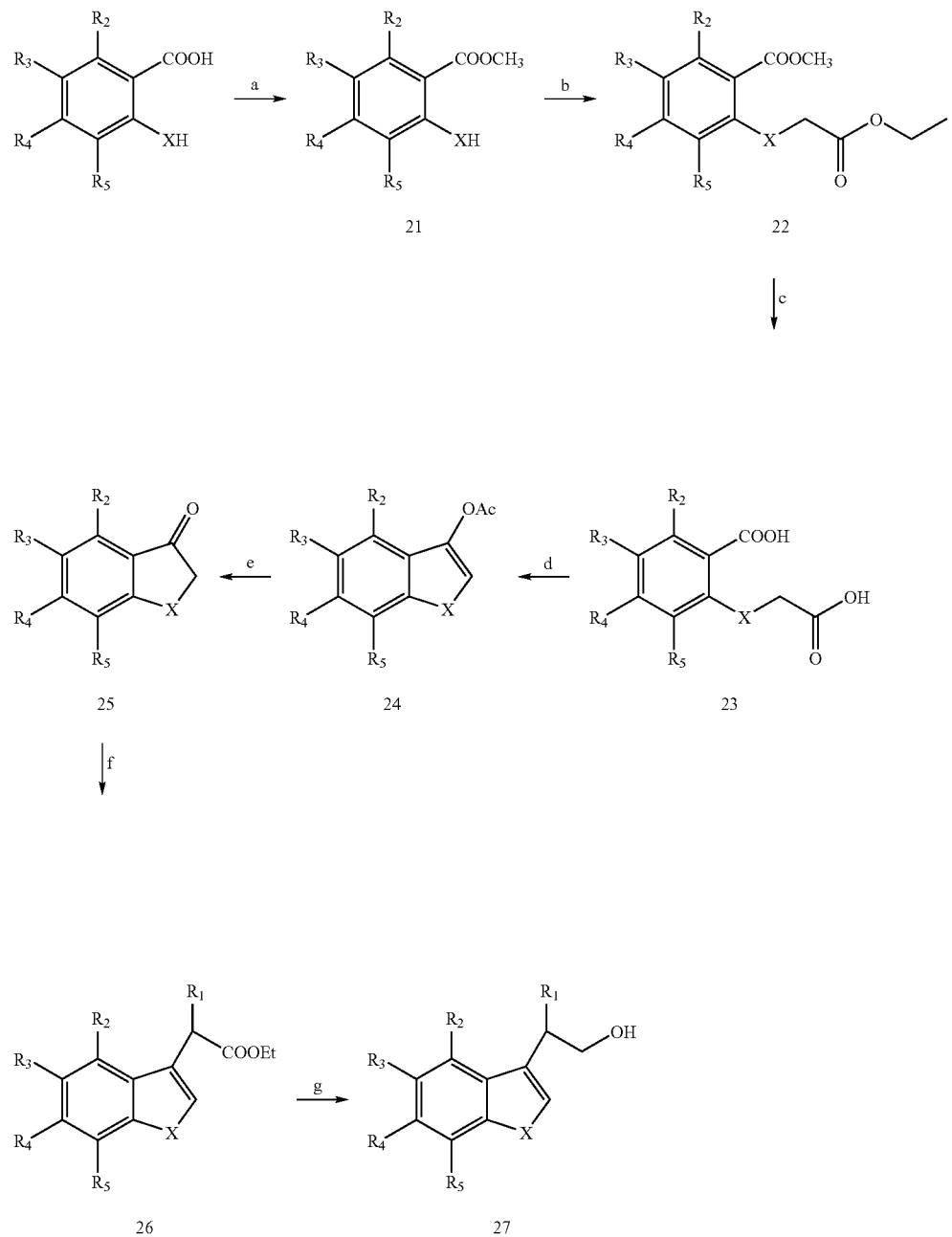
(a) MeOH. HCl/ Reflux;
(b) BrCH₂COOEt/ K₂CO₃/ Acetone/ Reflux;
(c) NaOH/ EtOH/ THF/ Reflux;
(d) (CH₃CO)₂O/ CH₃COONa/ CH₃COOH/ reflux;
(e) 1N. HCl/ MeOH/ reflux;
(f) Ph₃P=CHR₁COOEt/ Toluene/ Reflux;
(g) LAH/ THF/ 0° C.

Compound 17 can be prepared from the commercially available imidazo[1,2-a]pyridine as outlined in Scheme 4.

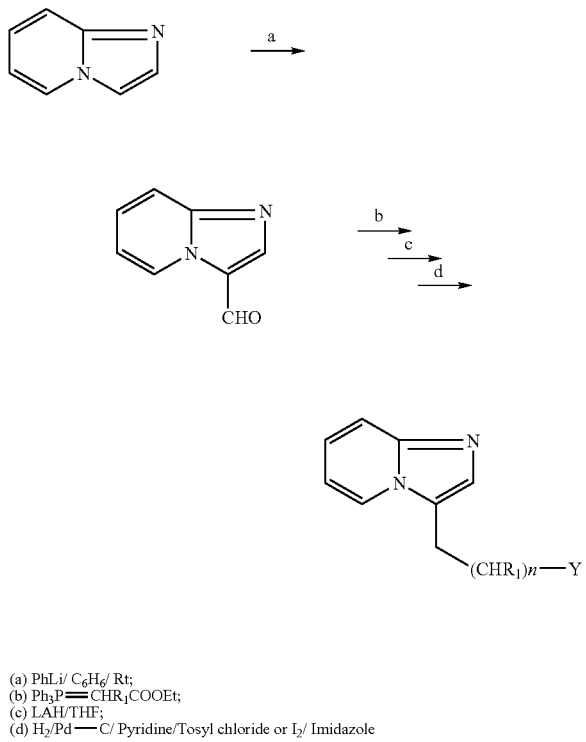

(a) PhLi/ C$_6$H$_6$/ Rt;
(b) Ph$_3$P=CHR$_1$COOEt;
(c) LAH/THF;
(d) H$_2$/Pd—C/ Pyridine/Tosyl chloride or I$_2$/ Imidazole Imidazo[1,2-a]pyridine was lithiated using PhLi and the resulting 3-lithio derivative was quenched with DMF to yield the 3-formyl derivative. This can be converted into 17 by Wittig reaction.

Alternatively compound 25 can be reacted with 1-triphenylphosphoranylidene-2-propanone 28 to yield 29, which can be reacted with 3-(1,2,3,6-tetrahydro-4-pyridinyl)1-H-indole derivatives 13 using sodium triacetoxyborohydride to give 30 (Scheme 5).

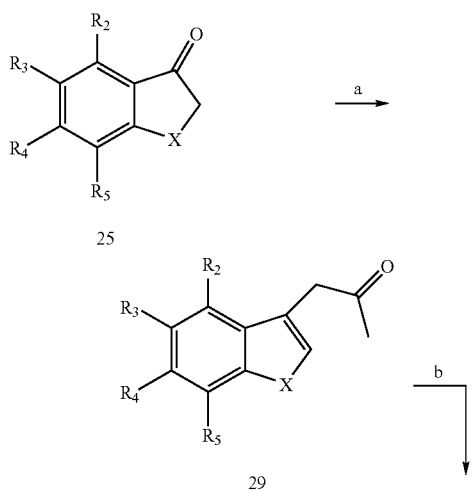

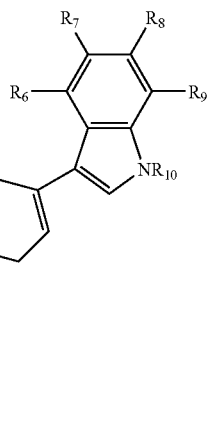

(a) Ph$_3$P=CHCOCH$_3$/Toluene/Reflux
(b) Reductive amination using sodium triacetoxyborohydride The terms "effective amount", "therapeutically effective amount" and "effective dosage" as used herein, refer to the amount of a compound of formula I that, when administered to a patient, is effective to at least partially ameliorate a condition from which the patient is suspected to suffer. Such conditions include serotonin disorders, including, but are not limited to, depression, anxiety, cognitive deficits, such as those resulting from Alzheimer's disease and other neurodegenerative disorders, schizophrenia, prostate cancer, and nicotine withdrawal.

The term "pharmaceutically acceptable salt", as used herein, refers to salts derived from organic and inorganic acids such as, for example, lactic, citric, acetic, cinnamic, tartaric, succinic, maleic, malonic, mandelic, malic, oxalic, propionic, fumaric, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Where $R_1$ to $R_9$ and $R_{11}$ contain a carboxyl group, salts of the compounds of this invention may be formed with bases such as alkali metals (Na, K, Li) or the alkaline earth metals (Ca or Mg).

The term "patient", as used herein, refers to a mammal, preferably a human.

The terms "administer", "administering" or "administration", as used herein, refer to either directly administering a compound or composition to a patient, or administering a prodrug derivative or analog of the compound, to the patient, which will form an equivalent amount of the active compound or substance within the patient's body.

The terms "in combination with", and "co-administer" refer, in certain embodiments, to the concurrent administration to a patient of SSRIs and the compounds of formula (I). When administered in combination, each component may be administered at the same time or sequentially in any order at different points in time. Thus, each component may be administered separately but sufficiently closely in time so as to provide the desired therapeutic effect.

As used herein, "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

As used herein, "stereoisomers" refers to compounds that have identical chemical constitution, but differ as regards the arrangement of the atoms or groups in space.

Compounds of formula I have been found to have affinity for the 5-HT reuptake transporter. They are therefore useful in the prevention and/or treatment of diseases affected by disorders of the serotonin affected neurological systems, such as depression and anxiety. The present invention accordingly provides pharmaceutical compositions that include the compound of formula I; and optionally one or more pharmaceutically-acceptable carriers, excipients, or diluents. The term "carrier", as used herein, shall encompass carriers, excipients and diluents.

Examples of such carriers are well know to those skilled in the art and are prepared in accordance with acceptable pharmaceutical procedures, such as, for example, those described in *Remington's Pharmaceutical Sciences*, 17th edition, ed. Alfonso R. Gennaro, Mack Publishing Company, Easton, Pa. (1985), which is incorporated herein by reference in its entirety. Pharmaceutical acceptable carriers are those carriers that are compatible with the other ingredients in the formulation and are biologically acceptable.

The compounds of formula I can be administered orally or parenterally, neat, or in combination with conventional pharmaceutical carriers. Representative solid carriers include one or more substances that can act as flavoring agents, lubricants, solubilizers, suspending agents, fillers, glidants, compression aids, binders, tablet-disintegrating agents, or encapsulating materials. They are formulated in conventional manner, for example, in a manner similar to that use for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid that is in admixture with the finely divided active ingredient. In tablets, the active ingredient is mixed with a carrier having the necessary compression properties in suitable proportion and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, microcrystalline cellulose, methyl cellulose, sodium carboxymethyl cellulose, carboxymethylcellulose calcium, polyvinylpyrrolidine, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, starches, sugars, low melting waxes, and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

Liquid carriers can be used in preparing solutions, suspensions, emulsions, syrups, and elixirs. The active ingredient can be dissolved or suspended in a pharmaceutically acceptable oil or fat. The liquid carrier can obtain other suitable pharmaceutical additives such as, for example, solubilizers, emulsifiers, buffers, preservatives, sweeteners, flavoring agents, suspending agents, thickening agents, colors, viscosity regulators, stablizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal, or subcutaneous injection. Sterile solutions can also be administered intravenously. Compositions for oral administration may be in either liquid or solid form.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

When administered for the prevention and/or treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic applications, compounds of formula I are provided to a patient already suffering from a disease in an amount sufficient to cure, or at least partially ameliorate, the symptoms of the disease and its complications. An amount adequate to accomplish this is defined as a "therapeutically effective amount". The dosage to be used in the prevention and/or treatment of a specific case must be subjectively determined by the attending physician. The variables involved include the specific condition and the weight, age, and response pattern of the patient. Effective administration of the compounds of this invention may be given at an oral dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. The projected daily dosages are expected to vary with route of administration.

Such doses may be administered in any manner useful in directing the active compounds herein to the patient's bloodstream, including orally, via implants, parentally (including intravenous, intraperitoneal, intraarticularly and subcutaneous injections), rectally, intranasally, topically, ocularly (via eye drops), vaginally, and transdermally.

In some cases it may be desirable to administer the compounds directly to the airways in the form of an aerosol. For administration by intranasal or intrabrochial inhalation, the compounds of formula I can be formulated into an aqueous or partially aqueous solution.

The compounds of this invention may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of formula I can also be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes containing absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

The compounds of formula I may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs of compounds of formula I. The term "prodrug", as used herein, is intended to include any covalently bonded carriers which release the active parent drug, for example, as according to formula I or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

Various forms of prodrugs are known in the art such as those discussed in, for example, Bundgaard (ed.), Design of Prodrugs, Elsevier (1985); Widder, et al. (ed.), Methods in Enzymology, vol. 4, Academic Press (1985); Krogsgaard-Larsen, et al., (ed.), "Design and Application of Prodrugs, Textbook of Drug Design and Development, Chapter 5, 113–191 (1991); Bundgaard, et al., *Journal of Drug Delivery Reviews,* 8:1–38 (1992); Bundgaard, *Journal of Pharmaceutical Sciences,* 77:285 et seq. (1988); Higuchi and Stella (eds.), Prodrugs as Novel Drug Delivery Systems, American Chemical Society (1975), each of which is incorporated by reference in its entirety.

The present invention further provides a compound of the invention for use as an active therapeutic substance. Compounds of formula I are of particular use in the prevention and/or treatment of diseases affected by disorders of serotonin.

The present invention further provides a compound of the invention in combination with a SSRI for use as an active therapeutic substance.

The present invention further provides a method of preventing and/or treating depression and anxiety in mammals including man, which comprises administering to the afflicted mammal an effective amount of a compound or a pharmaceutical composition of the invention.

The present invention further provides a method of preventing and/or treating depression and anxiety in mammals including man, which comprises co-administering to the afflicted mammal an effective amount of a compound or a pharmaceutical composition of the invention in combination with a SSRI.

EXAMPLES

Example 1

Preparation of 3-{1-[2-(1-benzofuran-3-yl)ethyl]-1,2,3,6-tetrahydro-4-pyridinyl}-1H-indole ("Compound 1")

Step 1: To a stirred solution of methyl salicylate (15.2 g, 0.1 mol) and anhydrous potassium carbonate (50.0 g, excess) in acetone (500 ml), ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous $MgSO_4$ and filtered. It was concentrated and taken to next step without any purification. White oil; Yield: 22.0 g (92%); 239 (M+H).

Step 2: The methyl-2-(ethoxy-2-oxoethoxy)benzoate obtained from step 1, (11.9 g, 50 mmol) was dissolved in THF:MeOH (1:1) (300 ml) and 5N NaOH (100 ml) was added. The reaction mixture was refluxed for 24 hrs and cooled to room temperature. At the end, it was concentrated to dryness and dissolved in water. The aqueous layer was acidified with con. HCl and the separated solid was filtered. It was washed well with water and dried. The product was taken to step without any purification. White solid; Yield: 9.0 g (91%); mp: 125–128° C.; 197 (M+H).

Step 3: The 2-(carboxymethoxy)-benzoic acid compound obtained from step 2 (9.8 g, 50 mmol) was dissolved in acetic anhydride (100 ml) and anhydrous sodium acetate (10.0 g, excess) was added. The reaction mixture was heated to 150° C. for 4 hrs. During this time, the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, benzofuran-3 (2H)-one, precipitated from the reaction mixture. It was filtered and washed well with water. It was dried at 40° C. and used for the next step without further purifications.

Yield: 3.5 g (51%); 135 (M+H).

Step 4: A mixture of benzofuran-3 (2H)-one (1.34 g, 10 mmol) and (carboxymethylene) triphenylphosphorane (5.22 g, 15 mmol) was refluxed in toluene (100 ml) for 48 hrs. At the end, reaction mixture was concentrated and loaded over a silica-gel column. The column was eluted with hexane (500 ml) and later with 25% ethyl acetate. The product, ethyl(-1-benzofuran-3-yl)acetate, was obtained as a white oil. Yield: 2.0 g (98%); 205 (M+H).

Step 5: To a stirred suspension of $LiAlH_4$ (200 mg, excess) in THF at 0° C., ethyl(-1-benzofuran-3-yl)acetate (1.02 g, 5 mmol) in THF (20 mL) was added slowly. After the addition, the reaction mixture was stirred at room temperature for 1 hr and quenched with saturated $NH_4Cl$ solution. The product was extracted with chloroform and washed well with water. It was dried over anhydrous $MgSO_4$; filtered and concentrated. The product, 2-(1-benzofuran-3-yl)ethanol, was obtained as a white oil and was pure enough to be taken to the next step without purification. Yield: 800 mg (98%); 163 (M+H).

Step 6: To a stirred solution of 2-(1-benzofuran-3-yl) ethanol (815 mg, 5 mmol) in anhydrous pyridine (20 ml), p-toluenesulfonyl chloride (1.14 g, 6.0 mmol) was added. The reaction mixture was kept at 0° C. for 48 hrs and quenched with ice cold water. The reaction mixture was extracted with chloroform, washed well with water and dried over anhydrous $MgSO_4$. It was filtered and concentrated. The crude product obtained was taken to next step without any purification.

A mixture of tosylate (316 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous $MgSO_4$ and concentrated to dryness. The dark colored solid was purified by silica-gel column chromatography by eluting it with 70% ethyl acetae:hexane. 3-{1-[2-(1-benzofuran-3-yl)ethyl]-1,2,3,6-tetrahydro-4-pyridinyl}-1H-indole was isolated as yellow solid; mp:166° C.; Yield: 150 mg (43%); 343 (M+H); $^1$H NMR: δ 8.12 (□□broad s, 1H), 7.92 (d,1H), 7.65–7.2, (m, 8H), 6.3 (m, 1H), 3.3 (bs, 2H), 2.98 (m, 2H), 2.8 (m, 4H), 2.6 (m, 2H).

Example 2

Preparation of 3-{1-[2-(1-benzofuran-3-yl)ethyl]-1,2,3,6-tetrahydro-4-pyridinyl}-1-methyl-1H-indole ("Compound 2")

3-{1-[2-(1-benzofuran-3-yl)ethyl]-1,2,3,6-tetrahydro-4-pyridinyl}-1H-indole (342 mg, 1 mmol) (obtained from example 1, step 6) in dry THF (50 ml) was slowly added to a stirred suspension of hexane and washed with 60% sodium hydride (44 mg) at 0° C. After the addition, the reaction mixture was stirred for 30 min and methyl iodide (213 mg, 1.5 mmol) was added. The reaction mixture was stirred for 4 hrs and quenched carefully with ice cold water. The reaction mixture was extracted with chloroform; washed well with water; dried over anhydrous $MgSO_4$; filtered and concentrated. The residue obtained was purified by silica-gel column chromatography by eluting it with 50% ethyl acetate:hexane. Light green semi-solid. Yield: 280 mg (78%); 357 (M+H); $^1$H NMR: δ□7.94 (d, 1H), 7.6 9 (d, 1H), 7.5–7.0 (m, 8H), 6.2 (bs, 1H), 3.8 (s, 3H), 3.49 (bs, 2H), 3.0 (m, 2H), 2.85 (m, 4H), 2.6 (bs, 2H).

Example 3

Preparation of 3-{1-[2-(1-benzofuran-3-yl)ethyl]-1,2,3,6-tetrahydro-4-pyridinyl}-7-ethyl-1H-indole ("Compound 3")

3-{1-[2-(1-benzofuran-3-yl)ethyl]-1,2,3,6-tetrahydro-4-pyridinyl}-7-ethyl-1H-indole was prepared by generally following the procedure outlined in example 1, step 6, starting from the tosylate (316 mg, 1 mmol) and 3 (1,2,3,6-tetrahydro-4-pyridinyl)-7-ethyl-1H-indole (226 mg, 1 mmol). The product was purified by silica-gel column chromatography by eluting it with 70% ethyl acetate:hexane. Brown oil; Yield: 210 mg (56%); 371 (M+H); $^1$HNMR (400 MHz, CDCl13): δ 8.05 (broad s, 1H, NH); 7.77~6.90 (m, 9H); 6.20 (s,1H); 3.36~2.60 (m, 12H); 1.39~1.35 (t, J=7.6 Hz, 3H).

Example 4

Preparation of 3-{1-[2-(1-benzofuran-3-yl)ethyl]-1,2,3,6-tetrahydro-4-pyridinyl}-6-fluoro-1H-indole ("Compound 4")

3-{1-[2-(1-benzofuran-3-yl)ethyl]-1,2,3,6-tetrahydro-4-pyridinyl}-6-fluoro-1H-indole was prepared by generally following the procedure outlined in example 1, step 6, starting from the tosylate (316 mg, 1 mmol) and 3 (1,2,3,6-tetrahydro-4-pyridinyl)-6-fluoro-1H-indole (216 mg, 1 mmol). The product was purified by silica-gel column chromatography by eluting it with 70% ethyl acetate:hexane. Brown oil; Yield: 180 mg (50%); 361 (M+H); $^1$H NMR δ 9.9 (broad s, 1H); 7.93~7.1 (m, 9H); 6.2 (s, 1H); 3.46~2.48 (m, 10H).

Example 5

Preparation of 3-{1-[2-(1-benzofuran-3-yl)ethyl]-1,2,3,6-tetrahydro-4-pyridinyl}-5-cyano-1H-indole ("Compound 5")

3-{1-[2-(1-benzofuran-3-yl)ethyl]-1,2,3,6-tetrahydro-4-pyridinyl}-5-cyano-1H-indole was prepared by generally following the procedure outlined in example 1, step 6, starting from the tosylate (316 mg, 1 mmol) and 3 (1,2,3,6-tetrahydro-4-pyridinyl)-5-cyano-1H-indole (213 mg, 1 mmol). The product was purified by silica-gel column chromatography by eluting it with 80% ethyl acetate:hexane. Brown solid; Yield: 239 mg (65%); 369 (M+H); H NMR: δ $^1$HNMR (400 MHz, CDCl$_3$): δ8.49 (broad, s, 1H, NH); 7.69~6.99 (m, 9H); 6.18~6.17 (s, 1H); 3.36~2.46 (m, 10H).

Example 6

Preparation of 3-{1-[2-(1-benzofuran-3-yl)ethyl]-1,2,3,6-tetrahydro-4-pyridinyl}-5-fluoro-1H-indole ("Compound 6")

3-{1-[2-(1-benzofuran-3-yl)ethyl]-1,2,3,6-tetrahydro-4-pyridinyl}-5-fluoro-1H-indole was prepared by generally following the procedure outlined in example 1, step 6, starting from the tosylate (316 mg, 1 mmol) and 3 (1,2,3,6-tetrahydro-4-pyridinyl)-5-fluoro-1H-indole (216 mg, 1 mmol). The product was purified by silica-gel column chromatography by eluting it with 80% ethyl acetate:hexane. Brown solid; Yield: 60 mg (16%); 361(M+H); $^1$H NMR: δ (400 MHz, CDCl$_3$): δ10.2 (broad s, 1H, NH); 7.82~6.93 (m, 9H); 6.07 (s,1H); 3.48~2.50 (m, 10H).

Example 7

Preparation of 3-{1-[2-(6-chloro-1-benzofuran-3-yl)ethyl]-1,2,3,6-tetrahydro-4-pyridinyl}-1H-indole ("Compound 7")

Step 1: To a stirred solution of methyl-4-chloro-2-hydroxy-benzoate (18.6 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous MgSO$_4$ and filtered. It was concentrated and taken to next step without any purification. White oil; Yield: 27.0 g (99%); 273 (M+H).

Step 2: The methyl-2-(ethoxy-2-oxoethoxy)-4-chloro-benzoate obtained from step 1, (13.6 g, 50 mmol) was dissolved in THF:MeOH (1:1) (300 ml) and 5N NaOH (100 ml) was added. The reaction mixture was refluxed for 24 hrs and cooled to room temperature. At the end it was concentrated to dryness and dissolved in water. The aqueous layer was acidified with con. HCl and the separated solid were filtered. It was washed well with water and dried. The product was taken to step without any purification. White solid; Yield: 10.0 g (86%); 231 (M+H).

Step 3: The 2-(carboxymethoxy)-4-chloro-benzoic acid compound obtained from step 2 (11.5 g, 50 mmol) was dissolved in acetic anhydride (100 ml) and anhydrous sodium acetate (10.0 g, excess) was added. The reaction mixture was heated to 150° C. for 4 hrs. During this time the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, 6-chloro-benzofuran-3 (2H)-one, precipitated from the reaction mixture. It was filtered and washed well with water. It was dried at 40° C. and used for the next step without further purifications. Yield: 5.8 g (69%); 169 (M+H).

Step 4: A mixture of 6-chloro-benzofuran-3 (2H)-one (1.68 g, 10 mmol) and (carboxymethylene)triphenylphosphorane (5.22 g, 15 mmol) was refluxed in toluene (100 ml) for 48 hrs. At the end, the reaction mixture was concentrated and loaded over a silica-gel column. The column was eluted with hexane (500 ml) and later with 25% ethyl acetate. The product, ethyl(6-chloro-1-benzofuran-3-yl)acetate, was obtained as a white oil. Yield: 2.1 g (87%); 239 (M+H).

Step 5: To a stirred suspension of LiAlH$_4$ (200 mg, excess) in THF at 0° C., ethyl(6-chloro-1-benzofuran-3-yl) acetate (1.19 g, 50 mmol) in THF (20 mL) was added slowly. After the addition, the reaction mixture was stirred at room temperature for 1 hr and quenched with saturated NH$_4$Cl solution. The product was extracted with chloroform and washed well with water. It was dried over anhydrous MgSO$_4$; filtered and concentrated. The product, 2-(6-chloro-1-benzofuran-3-yl)ethanol, was obtained as a white oil pure enough to be taken to the next step without purification. Yield: 900 mg (91%); 197 (M+H).

Step 6: To a stirred solution of 2-(6-chloro-1-benzofuran-3-yl)ethanol (980 mg, 5 mmol) in anhydrous pyridine (20 ml), p-toluenesulfonyl chloride (1.14 g, 6.0 mmol) was added. The reaction mixture was kept at 0° C. for 48 hrs and quenched with ice cold water. The reaction mixture was extracted with chloroform, washed well with water and dried over anhydrous MgSO$_4$. It was filtered and concentrated. The crude product obtained was taken to next step without any purification.

A mixture of tosylate (350 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous MgSO$_4$ and concentrated to dryness. The dark colored solid was purified by silica-gel column chromatography by eluting it with 70% ethyl acetae:hexane. 3-{1-[2-(6-chloro-1-benzofuran-3-yl)ethyl]-1,2,3,6-tetrahydro-4-pyridinyl}-1H-indole was isolated as yellow oil; Yield: 220 mg (58%); 377 (M+H); $^1$HNMR (400 MHz, CDCl$_3$): δ10.2 (broad s, 1H, NH); 7.82~7.01 (m, 9H); 6.14 (s, 1H); 3.32~2.49 (m, 10H).

Example 8

Preparation of 3-{1-[2-(6-chloro-1-benzofuran-3-yl)ethyl]-1,2,3,6-tetrahydro-4-pyridinyl}-5-fluoro-1H-indole ("Compound 8")

3-{1-[2-(6-chloro-1-benzofuran-3-yl)ethyl]-1,2,3,6-tetrahydro-4-pyridinyl}-5-fluoro-1H-indole was prepared by generally following the procedure outlined in example 7, step 6, starting from the tosylate (350 mg, 1 mmol) and 3 (1,2,3,6-tetrahydro-4-pyridinyl)-5-fluoro-1H-indole (216 mg, 1 mmol). The product was purified by silica-gel column chromatography by eluting it with 80% ethyl acetate:hexane. Brown solid; Yield: 189 mg (47%); 395 (M+H); $^1$HNMR (400 MHz, CDCl$_3$): δ10.2 (broad s, 1H, NH); 7.90~6.92 (m, 7H); 6.07 (s, 1H); 3.32~2.49 (m, 11H).

Example 9

Preparation of 3-{1-[2-(6-chloro-1-benzofuran-3-yl)ethyl]-1,2,3,6-tetrahydro-4-pyridinyl}-6-fluoro-1H-indole ("Compound 9")

3-{1-[2-(6-chloro-1-benzofuran-3-yl)ethyl]-1,2,3,6-tetrahydro-4-pyridinyl}-6-fluoro-1H-indole was prepared by generally following the procedure outlined in example 7, step 6, starting from the tosylate (350 mg, 1 mmol) and 3 (1,2,3,6-tetrahydro-4-pyridinyl)-6-fluoro-1H-indole (216 mg, 1 mmol). The product was purified by silica-gel column chromatography by eluting it with 80% ethyl acetate:hexane. Brown solid; Yield: 135 mg (34%); 395 (M+H); $^1$HNMR (400 MHz, CDCl$_3$): δ 8.5 (broad, s, 1H, NH); 7.81~6.80 (m, 7H); 6.20 (s, 1H); 3.40~2.60 (m, 11H).

Example 10

Preparation of 3-{1-[2-(6-methoxy-1-benzofuran-3-yl)ethyl]-1,2,3,6-tetrahydro-4-pyridinyl}-1H-indole ("Compound 10")

Step 1: To a stirred solution of methyl-4-methoxy-2-hydroxy-benzoate (18.2 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous MgSO$_4$ and filtered. It was concentrated and taken to next step without any purification. White oil; Yield: 24.0 g (89%); 269 (M+H).

Step 2: The methyl-2-(ethoxy-2-oxoethoxy)-4-methoxy-benzoate obtained from the step 1, (13.4 g, 50 mmol) was dissolved in THF:MeOH (1:1) (300 ml) and 5N NaOH (100 ml) was added. The reaction mixture was refluxed for 24 hrs and cooled to room temperature. At the end it was concentrated to dryness and dissolved in water. The aqueous layer was acidified with con. HCl and the separated solid were filtered. It was washed well with water and dried. The product was taken to step without any purification. White solid; Yield: 8.5 g (75%); 227 (M+H).

Step 3: The 2-(carboxymethoxy)-4-methoxy-benzoic acid compound obtained from the step 2 (11.3 g, 50 mmol) was dissolved in acetic anhydride (100 ml) and anhydrous sodium acetate (10.0 g, excess) was added. The reaction mixture was heated to 150° C. for 4 hrs. During this time the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, 6-methoxy-benzofuran-3 (2H)-one precipitated from the reaction mixture. It was filtered and washed well with water. It was dried at 40° C. and used for the next step without further purifications. Yield: 4.7 g (57%); 165 (M+H).

Step 4: A mixture of 6-methoxy-benzofuran-3 (2H)-one (1.64 g, 10 mmol) and (carboxymethylene)triphenylphosphorane (5.22 g, 15 mmol) was refluxed in toluene (100 ml) for 48 hrs. At the end, reaction mixture was concentrated and loaded over silica-gel column. The column was eluted with hexane (500 ml) and later with 25% ethyl acetate. The product, ethyl(6-methoxy-1-benzofuran-3-yl)acetate was obtained as a white oil. Yield: 1.8 g (76%); 235 (M+H).

Step 5: To a stirred suspension of LiAlH$_4$ (200 mg, excess) in THF at 0° C., ethyl(6-methoxy-1-benzofuran-3-yl)acetate (1.17 g, 5 mmol) in THF (20 ml) was added slowly. After the addition, the reaction mixture was stirred at room temperature for 1 hr and quenched with saturated NH$_4$Cl solution. The product was extracted with chloroform and washed well with water. It was dried over anhydrous MgSO$_4$; filtered and concentrated. The product, 2-(6-methoxy-1-benzofuran-3-yl)ethanol was obtained as a white oil and was pure enough to be taken to the next step without purification. Yield: 850 mg (88%); 193 (M+H).

Step 6: To a stirred solution of 2-(6-methoxy-1-benzofuran-3-yl)ethanol (960 mg, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. It was then extracted with chloroform, washed well with 5% NaS$_2$O$_3$ solution and the organic layer was dried over anhydrous MgSO$_4$. It was filtered and concentrated. The residue was purified by silica-gel column chromatography by eluting it with 30% ethyl acetate:hexane. The product, namely 2-(6-methoxy-1-benzofuran-3-yl)ethyl iodide, was obtained as brown liquid; Yield: 1.2 g (80%); 302 (M+H).

A mixture of 2-(6-methoxy-1-benzofuran-3-yl)ethyl iodide (301 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous MgSO$_4$ and concentrated to dryness. The dark colored solid was purified by silica-gel column chromatography by eluting it with 70% ethyl acetae:hexane. 3-{1-[2-(6-methoxy-1-benzofuran-3-yl)ethyl]-1,2,3,6-tetrahydro-4-pyridinyl}-1H-indole was isolated as yellow oil; Yield: 180 mg (48%); 373 (M+H); $^1$H NMR: δ 8.6 (d, 1H), 8.25 (bs, 1H), 7.9 (d,1H), 7.6–6.9 (m, 7H), 6.23 (bs, 1H), 3.85 (s, 3H), 3.5 (m,2H), 3.0 (m, 2H), 2.8 (m, 4H), 2.65 (m, 2H).

Example 11

Preparation of 3-{1-[2-(6-methoxy-1-benzofuran-3-yl)ethyl]-1,2,3,6-tetrahydro-4-pyridinyl}-5-fluoro-1H-indole ("Compound 11")

3-{1-[2-(6-methoxy-1-benzofuran-3-yl)ethyl]-1,2,3,6-tetrahydro-4-pyridinyl}-5-fluoro-1H-indole was prepared by generally following the procedure outlined in example 10, step 6, starting from the of 2-(6-methoxy-1-benzofuran-3-yl)ethyl iodide (301 mg, 1 mmol) and 3 (1,2,3,6-tetrahydro- 4-pyridinyl)-5-fluoro-1H-indole (216 mg, 1 mmol). The product was purified by silica-gel column chromatography by eluting it with 80% ethyl acetate:hexane. Brown solid; Yield: 178 mg (45%); 391 (M+H); $^1$HNMR (400 MHz, CDCl$_3$):δ 8.50 (broad, s, 1H, NH); 7.81~6.80 (m, 7H); 6.20 (s, 1H); 3.67 (s, 3H); 3.40~2.60 (m, 11H).

Example 12

Preparation of 3-{1-[2-(6-methoxy-1-benzofuran-3-yl)ethyl]-1,2,3,6-tetrahydro-4-pyridinyl}-6-fluoro-1H-indole ("Compound 12")

3-{1-[2-(6-methoxy-1-benzofuran-3-yl)ethyl]-1,2,3,6-tetrahydro-4-pyridinyl}-6-fluoro-1H-indole was prepared by following the procedure outlined in example 10, step 6, starting from the of 2-(6-methoxy-1-benzofuran-3-yl)ethyl iodide (301 mg, 1 mmol) and 3 (1,2,3,6-tetrahydro-4-pyridinyl)-6-fluoro-1H-indole (216 mg, 1 mmol). The product was purified by silica-gel column chromatography by eluting it with 80% ethyl acetate:hexane. Brown solid; Yield: 180 mg (46%); 391 (M+H); $^1$HNMR (400 MHz, CDCl$_3$): δ8.50 (broad s, 1H, NH); 7.81~6.80 (m, 7H); 6.2 (s, 1H); 3.67 (s, 3H); 3.40~2.60 (m, 11H).

Example 13

Preparation of 3-{1-[2-(6-methoxy-1-benzofuran-3-yl)ethyl]-1,2,3,6-tetrahydro-4-pyridinyl}-6-cyano-1H-indole ("Compound 13")

3-{1-[2-(6-methoxy-1-benzofuran-3-yl)ethyl]-1,2,3,6-tetrahydro-4-pyridinyl}-6-fluoro-1H-indole was prepared by generally following the procedure outlined in example 10, step 6, starting from the of 2-(6-methoxy-1-benzofuran-3-yl)ethyl iodide (301 mg, 1 mmol) and 3 (1,2,3,6-tetrahydro-4-pyridinyl)-6-fluoro-1H-indole (216 mg, 1 mmol). The product was purified by silica-gel column chromatography by eluting it with 80% ethyl acetate:hexane. Brown solid; mp181° C.; Yield: 250 mg (62%); 398 (M+H); $^1$H NMR: δ 9.50 (broad, s, 1H,); 8.2~6.80 (m, 7H); 6.20 (s, 1H); 3.89 (m, 2H); 3.65 m, 2H), 3.55 m,2H), 2.60 (m, 4H).

Example 14

Preparation of 3-{1-[2-(5-chloro-1-benzofuran-3-yl)ethyl]-1,2,3,6-tetrahydro-4-pyridinyl}-1H-indole ("Compound 14")

Step 1: To a stirred solution of methyl-5-chloro-2-hydroxybenzoate (18.6 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous MgSO$_4$ and filtered. It was concentrated and taken to next step without any purification. White oil; Yield: 22.0 g (80%); 273 (M+H).

Step 2: The methyl-2-(ethoxy-2-oxoethoxy)-5-chloro-benzoate obtained from the step 1, (13.6 g, 50 mmol) was dissolved in THF:MeOH (1:1) (300 ml) and 5N NaOH (100 ml) was added. The reaction mixture was refluxed for 24 hrs and cooled to room temperature. At the end it was concentrated to dryness and dissolved in water. The aqueous layer was acidified with con. HCl and the separated solid were filtered. It was washed well with water and dried. The product was taken to step without any purification. White solid; Yield: 8.0 g (69%); 231 (M+H).

Step 3: The 2-(carboxymethoxy)-5-chloro-benzoic acid compound obtained from the step 2 (11.5 g, 50 mmol) was dissolved in acetic anhydride (100 ml) and anhydrous sodium acetate (10.0 g, excess) was added. The reaction mixture was heated to 150° C. for 4 hrs. During this time the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, 5-chloro-benzofuran-3 (2H)-one, precipitated from the reaction mixture. It was filtered and washed well with water. It was dried at 40° C. and used for the next step without further purifications. Yield: 6.2 g (73%); 169 (M+H).

Step 4: A mixture of 5-chloro-benzofuran-3 (2H)-one (1.68 g, 10 mmol) and (carboxymethylene)triphenylphosphorane (5.22 g, 15 mmol) was refluxed in toluene (100 ml) for 48 hrs. At the end, reaction mixture was concentrated and loaded over a silica-gel column. The column was eluted with hexane (500 ml) and later with 25% ethyl acetate. The product, ethyl(5-chloro-1-benzofuran-3-yl)acetate, was obtained as a white oil. Yield: 1.8 g (75%); 239 (M+H).

Step 5: To a stirred suspension of LiAlH$_4$ (200 mg, excess) in THF at 0° C., ethyl(5-chloro-1-benzofuran-3-yl) acetate (1.19 g, 50 mmol) in THF (20 mL) was added slowly. After the addition, reaction mixture was stirred at room temperature for 1 hr and quenched with saturated NH$_4$Cl solution. The product was extracted with chloroform and washed well with water. It was dried over anhydrous MgSO$_4$; filtered and concentrated. The product, 2-(5-chloro-1-benzofuran-3-yl)ethanol, was obtained as a white oil pure enough to be taken to the next step without purification. Yield: 850 mg (86%); 197 (M+H).

Step 6: To a stirred solution of 2-(5-chloro-1-benzofuran-3-yl)ethanol (980 mg, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. It was extracted with chloroform, washed well with 5% Na$_2$S$_2$O$_3$ solution and the organic layer was dried over anhydrous MgSO$_4$. It was filtered and concentrated. The residue was purified by silica-gel column chromatography by eluting it with 30% ethyl acetate:hexane. The product, namely 2-(5-chloro-1-benzofuran-3-yl)ethyl iodide, was obtained as brown liquid; Yield: 1.2 g (80%); 306 (M+H).

A mixture of 2-(5-chloro-1-benzofuran-3-yl)ethyl iodide (305 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous MgSO$_4$ and concentrated to dryness. The dark colored solid was purified by silica-gel column chromatography by eluting it with 70% ethyl acetae:hexane. 3-{1-[2-(6-methoxy-1-benzofuran-3-yl)ethyl]-1,2,3,6-tetrahydro-4-pyridinyl}-1H-indole was isolated as brown solid. mp 54° C. Yield: 210 mg (55%); 377 (M+H); $^1$H NMR: δ 8.98 (broad, s, 1H,); 7.92~6.94 (m, 9H); 6.25 (s, 1H); 3.78 (bs, 2H); 3.60 (bs, 2H), 3.45 (bs, 2H), 3.25 (bs, 4H).

Example 15

Preparation of 3-{1-[2-(5-chloro-1-benzofuran-3-yl)ethyl]-1,2,3,6-tetrahydro-4-pyridinyl}-5-fluoro-1H-indole ("Compound 15")

3-{1-[2-(5-chloro-1-benzofuran-3-yl)ethyl]-1,2,3,6-tetrahydro-4-pyridinyl}-5-fluoro-1H-indole was prepared by generally following the procedure outlined in example 14, step 6, starting from the of 2-(5-chloro-1-benzofuran-3-yl) ethyl iodide (306 mg, 1 mmol) and 3 (1,2,3,6-tetrahydro-4-pyridinyl)-5-fluoro-1H-indole (216 mg, 1 mmol). The product was purified by silica-gel column chromatography by eluting it with 80% ethyl acetate:hexane. Brown solid; Yield: 120 mg (30%); 395 (M+H); $^1$HNMR (400 MHz, $CDCl_3$): δ8.57 (broad, s, 1H, NH); 2.56~6.96 (m, 7H); 6.10 (s, 1H); 3.35~2.50 (m, 1H).

Example 16

Preparation of 3-{1-[2-(5-chloro-1-benzofuran-3-yl)ethyl]-1,2,3,6-tetrahydro-4-pyridinyl}-6-fluoro-1H-indole ("Compound 16")

3-{1-[2-(5-chloro-1-benzofuran-3-yl)ethyl]-1,2,3,6-tetrahydro-4-pyridinyl}-5-fluoro-1H-indole was prepared by following the procedure outlined in example 14, step 6, starting from the of 2-(5-chloro-1-benzofuran-3-yl)ethyl iodide (306 mg, 1 mmol) and 3 (1,2,3,6-tetrahydro-4-pyridinyl)-6-fluoro-1H-indole (216 mg, 1 mmol). The product was purified by silica-gel column chromatography by eluting it with 80% ethyl acetate:hexane. Brown solid; Yield: 180 mg (45%); 395 (M+H); $^1$HNMR (400 MHz, $CDCl_3$):δ 8.74 (broad, s, 1H,); 7.80~6.70 (m, 7H); 6.20 (s, 1H); 3.50~2.60 (m, 10H).

Example 17

Preparation of 3-{1-[2-(5-fluoro-1-benzofuran-3-yl)ethyl]-1,2,3,6-tetrahydro-4-pyridinyl}-1H-indole ("Compound 17")

Step 1: To a stirred solution of 5-fluoro-2-hydroxy-methyl benzoate (17.0 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous $MgSO_4$ and filtered. It was concentrated and taken to next step without any purification. White oil; Yield: 23.0 g (89%); 257 (M+H).

Step 2: The methyl-5-fluoro-2-(ethoxy-2-oxoethoxy)benzoate obtained from step 1, (12.8 g, 50 mmol) was dissolved in THF:MeOH (1:1) (300 ml) and 5N NaOH (100 ml) was added. The reaction mixture was refluxed for 24 hrs and cooled to room temperature. At the end it was concentrated to dryness and dissolved in water. The aqueous layer was acidified with con. HCl and the separated solid were filtered. It was washed well with water and dried. The product was taken to step without any purification. White solid; Yield: 8.3 g (77%); 215 (M+H).

Step 3: The 2-(carboxymethoxy)-5-fluoro-benzoic acid compound obtained from the step 2 (10.7 g, 50 mmol) was dissolved in acetic anhydride (100 ml) and anhydrous sodium acetate (10.0 g, excess) was added. The reaction mixture was heated to 150° C. for 4 hrs. During this time, the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, 5-fluoro-benzofuran-3 (2H)-one, precipitated from the reaction mixture. It was filtered and washed well with water. It was dried at 40° C. and used for the next step without further purifications. Yield: 5.8 g (76%); 153 (M+H).

Step 4: A mixture of 5-fluoro-benzofuran-3 (2H)-one (1.52 g, 10 mmol) and (carboxymethylene)triphenylphosphorane (5.22 g, 15 mmol) was refluxed in toluene (100 ml) for 48 hrs. At the end, reaction mixture was concentrated and loaded over a silica-gel column. The column was eluted with hexane (500 ml) and later with 25% ethyl acetate. The product, ethyl(5-fluoro-1-benzofuran-3-yl)acetate, was obtained as a white oil. Yield: 1.8 g (80%); 223 (M+H).

Step 5: To a stirred suspension of $LiAlH_4$ (200 mg, excess) in THF at 0° C., ethyl(5-fluoro-1-benzofuran-3-yl) acetate (1.11 g, 5 mmol) in THF (20 mL) was added slowly. After the addition, the reaction mixture was stirred at room temperature for 1 hr and quenched with saturated $NH_4Cl$ solution. The product was extracted with chloroform and washed well with water. It was dried over anhydrous $MgSO_4$; filtered and concentrated. The product, 2-(5-fluoro-1-benzofuran-3-yl)ethanol obtained as white oil and was pure enough to be taken to the next step without purification. Yield: 820 mg (91%); 181 (M+H).

Step 6: To a stirred solution of 2-(5-fluoro-1-benzofuran-3-yl)ethanol (900 mg, 5 mmol) in anhydrous pyridine (20 ml), p-toluenesulfonyl chloride (1.14 g, 6.0 mmol) was added. The reaction mixture was kept at 0° C. for 48 hrs and quenched with ice cold water. The reaction mixture was extracted with chloroform, washed well with water and dried over anhydrous $MgSO_4$. It was filtered and concentrated. The crude product obtained was taken to next step without any purification. A mixture of tosylate (334 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous $MgSO_4$ and concentrated to dryness. The dark colored solid was purified by silica-gel column chromatography by eluting it with 70% ethyl acetate:hexane. 3-{1-[2-(5-fluoro-1-benzofuran-3-yl)ethyl]-1,2,3,6-tetrahydro-4-pyridinyl}-1H-indole was isolated as yellow solid. mp 158° C.; Yield: 140 mg (38%); 361 (M+H); $^1$H NMR: δ 8.2 (bs, 1H), 7.9 (d,1H), 7.59 (s, 1H), 7.45–7.0 (m, 7H), 6.3 9s, 1H), 3.4 (m, 2H), 3.0 (m, 2H), 2.84 (m, 4H), 2.68 (m, 2H).

Example 18

Preparation of 3-{1-[2-(5-fluoro-1-benzofuran-3-yl)ethyl]-1,2,3,6-tetrahydro-4-pyridinyl}-5-cyano-1H-indole ("Compound 18")

3-{1-[2-(5-fluoro-1-benzofuran-3-yl)ethyl]-1,2,3,6-tetrahydro-4-pyridinyl}-5-cyano-1H-indole was prepared by generally following the procedure outlined in example 17, step 6, starting from the tosylate (334 mg, 1 mmol) and 3 (1,2,3,6-tetrahydro-4-pyridinyl)-5-cyano-1H-indole (223 mg, 1 mmol). The product was purified by silica-gel column chromatography by eluting it with 80% ethyl acetate:hexane. Yellow solid; mp 259° C. (HCl salt); Yield:120 mg (31%); 386 (M+H).

Example 19

Preparation of 3-{1-[2-(5-fluoro-1-benzofuran-3-yl)ethyl]-1,2,3,6-tetrahydro-4-pyridinyl}-5-fluoro-1H-indole ("Compound 19")

3-{1-[2-(5-fluoro-1-benzofuran-3-yl)ethyl]-1,2,3,6-tetrahydro-4-pyridinyl}-5-fluoro-1H-indole was prepared by generally following the procedure outlined in example 17, step 6, starting from the tosylate (334 mg, 1 mmol) and 3 (1,2,3,6-tetrahydro-4-pyridinyl)-5-fluoro-1H-indole (216 mg, 1 mmol). The product was purified by silica-gel column chromatography by eluting it with 80% ethyl acetate:hexane. Dark semi-solid solid; Yield: 180 mg, (47%); 379, (M+H); $^1$H NMR: □δ□9.2 (bs, 1H), 8.8 (d, 11H), 8.3 (s, 1H), 8.2–6.8 (m, 6H), 6.2 (m, 1H), 3.9–3.0 (m, 10H).

Example 20

Preparation of 3-{1-[2-(7-methoxy-1-benzofuran-3-yl)ethyl]-1,2,3,6-tetrahydro-4-pyridinyl}-1H-indole ("Compound 20")

Step 1: A mixture of 7-methoxy-benzofuran-3 (2H)-one (1.64 g, 10 mmol) and (carboxymethylene)triphenylphosphorane (5.22 g, 15 mmol) was refluxed in toluene (100 ml) for 48 hrs. At the end, the reaction mixture was concentrated and loaded over silica-gel column. The column was eluted with hexane (500 ml) and later with 25% ethyl acetate. The product, ethyl(7-methoxy-1-benzofuran-3-yl)acetate was obtained as a white oil. Yield: 1.9 g (81%); 235 (M+H).

Step 2: To a stirred suspension of LiAlH$_4$ (200 mg, excess) in THF at 0° C., ethyl(7-methoxy-1-benzofuran-3-yl)acetate (1.17 g, 5 mmol) in THF (20 mL) was added slowly. After the addition, the reaction mixture was stirred at room temperature for 1 hr and quenched with saturated NH$_4$Cl solution. The product was extracted with chloroform and washed well with water. It was dried over anhydrous MgSO$_4$; filtered and concentrated. The product, 2-(7-methoxy-1-benzofuran-3-yl)ethanol obtained as a white oil, was pure enough and taken to the next step without purification. Yield: 800 mg (83%); 193 (M+H).

Step 3: To a stirred solution of 2-(7-methoxy-1-benzofuran-3-yl)ethanol (960 mg, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. The reaction mixture was extracted with chloroform, washed well with 5% Na$_2$S$_2$O$_3$ solution and the organic layer was dried over anhydrous MgSO$_4$. It was filtered and concentrated. The residue was purified by silica-gel column chromatography by eluting it with 30% ethyl acetate:hexane. The product, namely 2-(7-methoxy-1-benzofuran-3-yl)ethyl iodide, was obtained as brown liquid. Yield: 1.3 g (86%); 302 (M+H).

A mixture of 2-(7-methoxy-1-benzofuran-3-yl)ethyl iodide (301 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction was quenched with water and extracted with chloroform. The organic layer was washed with water and dried over anhydrous MgSO$_4$ and concentrated to dryness. The dark colored solid was purified by silica-gel column chromatography by eluting it with 70% ethyl acetae: hexane. 3-{1-[2-(7-methoxy-1-benzofuran-3-yl)ethyl]-1,2,3,6-tetrahydro-4-pyridinyl}-1H-indole was isolated as yellow solid. mp 156° C.; Yield: 80 mg (21%); 373 (M+H); $^1$H NMR: δ 8.4 (bs, 1H), 7.9 (d,1H), 7.5 (s, 1H), 7.35–6.80 (m, 7H), 6.2 (m,1H), 3.97 (s, 3H), 3.50 (m,2H), 3.19 (m, 2H), 2.93 (m, 4H), 2.67 (m, 2H).

Example 21

Preparation of 3-{1-[2-(7-methoxy-1-benzofuran-3-yl)ethyl]-1,2,3,6-tetrahydro-4-pyridinyl}-6-fluoro-1H-indole ("Compound 21")

3-{1-[2-(7-methoxy-1-benzofuran-3-yl)ethyl]-1,2,3,6-tetrahydro-4-pyridinyl}-6-fluoro-1H-indole was prepared by generally following the procedure outlined in example 20, step 3, starting from 2-(7-methoxy-1-benzofuran-3-yl)ethyl iodide (301 mg, 1 mmol) and 3 (1,2,3,6-tetrahydro-4-pyridinyl)-6-fluoro-1H-indole (216 mg, 1 mmol). The product was purified by silica-gel column chromatography by eluting it with 80% ethyl acetate:hexane. Brown solid; mp 136° C.; Yield: 120 mg (30%); 391 (M+H); $^1$H NMR: □δ□8.25 (bs, 1H), 7.8 (m,1H), 7.4 (s, 1H), 7.25 (s,1H), 7.3–6.80 (m, 5H), 6.17 (m,1H), 4.01 (s, 3H), 3.40 (m,2H), 3.02 (m, 2H), 2.93 (m, 4H), 2.65 (m, 2H).

Example 22

Preparation of 3-(1-[2-(7-methoxy-1-benzofuran-3-yl)ethyl]-1,2,3,6-tetrahydro-4-pyridinyl}-5-fluoro-1H-indole ("Compound 22")

3-{1-[2-(7-methoxy-1-benzofuran-3-yl)ethyl]-1,2,3,6-tetrahydro-4-pyridinyl}-5-fluoro-1H-indole was prepared by generally following the procedure outlined in example 20, step 3, starting from 2-(7-methoxy-1-benzofuran-3-yl)ethyl iodide (301 mg, 1 mmol) and 3 (1,2,3,6-tetrahydro-4-pyridinyl)-5-fluoro-1H-indole (216 mg, 1 mmol). The product was purified by silica-gel column chromatography by eluting it with 80% ethyl acetate:hexane. Brown solid; mp 171° C.; Yield: 60 mg (15%); 391 (M+H); $^1$H NMR: □δ□8.16 (bs, 1H), 7.6–7.5 (m,2H), 7.3–6.75 (m, 6H), 6.17 (m,1H), 4.01 (s, 3H), 3.35 (m,2H), 3.19 (m, 2H), 2.91 (m, 4H), 2.64 (m, 2H).

Example 23

Preparation of 3-{1-[2-(7-methoxy-1-benzofuran-3-yl)ethyl]-1,2,3,6-tetrahydro-4-pyridinyl}-5-cyano-1H-indole ("Compound 23")

3-{1-[2-(7-methoxy-1-benzofuran-3-yl)ethyl]-1,2,3,6-tetrahydro-4-pyridinyl}-5-cyano-1H-indole was prepared by generally following the procedure outlined in example 20, step 3, starting from 2-(7-methoxy-1-benzofuran-3-yl)ethyl iodide (301 mg, 1 mmol) and 3 (1,2,3,6-tetrahydro-4-pyridinyl)-5-cyano-1H-indole (223 mg, 1 mmol). The product was purified by silica-gel column chromatography by eluting it with 80% ethyl acetate:hexane. Brown solid; mp 72° C.; Yield: 50 mg (12%); 398 (M+H); $^1$H NMR (DMSO): □δ□11.2 (bs, 1H), 8.7 (d, 1H), 8.51 (s, 1H), 8.30 (s, 1H), 8.24 (s, 1H), 7.79–6.9 (m, 4H), 6.21 (m,1H), 3.92 (s, 3H), 3.23 (m,2H), 2.89 9m, 2H), 2.75 (m, 4H), 2.5 (m, 2H).

Example 24

Preparation of 3-{1-[2-(5-methoxy-1-benzofuran-3-yl)ethyl]-1,2,3,6-tetrahydro-4-pyridinyl}-1H-indole ("Compound 24")

Step 1: To a stirred solution of methyl-5-methoxy-2-hydroxy-benzoate (18.2 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous $MgSO_4$ and filtered. It was concentrated and taken to next step without any purification. Yellow oil; Yield: 21.0 g (78%); 269 (M+H).

Step 2: The methyl-2-(ethoxy-2-oxoethoxy)-5-methoxy-benzoate obtained from step 1, (13.4 g, 50 mmol) was dissolved in THF:MeOH (1:1) (300 ml) and 5N NaOH (100 ml) was added. The reaction mixture was refluxed for 24 hrs and cooled to room temperature. At the end it was concentrated to dryness and dissolved in water. The aqueous layer was acidified with con. HCl and the separated solid were filtered, washed well with water and dried. The product was taken to step without any purification. White solid; Yield: 10.2 g (90%); mp 150–153° C.; 227 (M+H).

Step 3: The 2-(carboxymethoxy)-5-methoxy-benzoic acid compound obtained from the step 2 (11.3 g, 50 mmol) was dissolved in acetic anhydride (100 ml) and anhydrous sodium acetate (10.0 g, excess) was added. The reaction mixture was heated to 150° C. for 4 hrs. During this time the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, 5-methoxy-benzofuran-3 (2H)-one, precipitated from the reaction mixture. It was filtered and washed well with water. It was dried at 40° C. and used for the next step without further purifications. Yield: 6.2 g (75%); 165 (M+H).

Step 4: A mixture of 5-methoxy-benzofuran-3 (2H)-one (1.64 g, 10 mmol) and (carboxymethylene)triphenylphosphorane (5.22 g, 15 mmol) was refluxed in toluene (100 ml) for 48 hrs. At the end, the reaction mixture was concentrated and loaded over silica-gel column. The column was eluted with hexane (500 ml) and later with 25% ethyl acetate. The product, ethyl(5-methoxy-1-benzofuran-3-yl)acetate, was obtained as a white oil. Yield: 1.6 g (68%); 235 (M+H).

Step 5: To a stirred suspension of $LiAlH_4$ (200 mg, excess) in THF at 0° C., ethyl(5-methoxy-1-benzofuran-3-yl)acetate (1.17 g, 5 mmol) in THF (20 mL) was added slowly. After the addition, reaction mixture was stirred at room temperature for 1 hr and quenched with saturated $NH_4Cl$ solution. The product was extracted with chloroform and washed well with water. It was dried over anhydrous $MgSO_4$; filtered and concentrated. The product, 2-(5-methoxy-1-benzofuran-3-yl)ethanol, obtained as white oil, was pure enough and taken to the next step without purification. Yellow oil; Yield: 900 mg (93%); 193 (M+H).

Step 6: To a stirred solution of 2-(5-methoxy-1-benzofuran-3-yl)ethanol (960 mg, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. It was extracted with chloroform, washed well with 5% $Na_2S_2O_3$ solution and the organic layer was dried over anhydrous $MgSO_4$. It was filtered and concentrated. The residue was purified by silica-gel column chromatography by eluting it with 30% ethyl acetate:hexane. The product, namely 2-(5-methoxy-1-benzofuran-3-yl)ethyl iodide, was obtained as brown liquid. Yield: 1.1 g (73%); 302 (M+H).

A mixture of 2-(5-methoxy-1-benzofuran-3-yl)ethyl iodide (301 mg, 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous $MgSO_4$ and concentrated to dryness. The dark colored solid was purified by silica-gel column chromatography by eluting it with 70% ethyl acetae: hexane. 3-{1-[2-(5-methoxy-1-benzofuran-3-yl)ethyl]-1,2,3,6-tetrahydro-4-pyridinyl}-1H-indole was isolated as yellow oil. Yield: 160 mg (43%); 373 (M+H); $^1$HNMR (400 MHz, $CDCl_3$): δ8.74 (broad, s, 1H, NH); 7.80~6.70 (m, 8H); 6.2 (s, 1H); 3.90 (s, 3H); 3.50~2.60 (m, 11H).

Example 25

Preparation of 3-{1-[2-(5-methoxy-1-benzofuran-3-yl)ethyl]-1,2,3,6-tetrahydro-4-pyridinyl}-5-fluoro-1H-indole ("Compound 25")

3-{1-[2-(5-methoxy-1-benzofuran-3-yl)ethyl]-1,2,3,6-tetrahydro-4-pyridinyl}-5-fluoro-1H-indole was prepared by generally following the procedure outlined in example 24, step 6, starting from 2-(5-methoxy-1-benzofuran-3-yl)ethyl iodide (301 mg, 1 mmol) and 3 (1,2,3,6-tetrahydro-4-pyridinyl)-5-fluoro-1H-indole (216 mg, 1 mmol). The product was purified by silica-gel column chromatography by eluting it with 80% ethyl acetate:hexane. Brown solid; Yield: 142 mg (36%); 391 (M+H); $^1$HNMR (400 MHz, $CDCl_3$):δ 8.63~8.61 (dd, J1=1.6 Hz, J2=1.6 Hz, 1H); 8.24~8.19 (s, 1H); 7.60~6.84 (m, 7H); 6.15~6.16 (s, 1H); 3.86~3.82 (s, 3H); 3.36~2.65) (m, 10H).

Example 26

Preparation of 3-{1-[2-(5-methoxy-1-benzofuran-3-yl)ethyl]-1,2,3,6-tetrahydro-4-pyridinyl}-6-fluoro-1H-indole ("Compound 26")

3-{1-[2-(5-methoxy-1-benzofuran-3-yl)ethyl]-1,2,3,6-tetrahydro-4-pyridinyl}-6-fluoro-1H-indole was prepared by generally following the procedure outlined in example 24, step 6, starting from 2-(5-methoxy-1-benzofuran-3-yl)ethyl iodide (301 mg, 1 mmol) and 3 (1,2,3,6-tetrahydro-4-pyridinyl)-6-fluoro-1H-indole (216 mg, 1 mmol). The product was purified by silica-gel column chromatography by eluting it with 80% ethyl acetate:hexane. Brown solid; Yield: 122 mg (31%); 391 (M+H); $^1$HNMR (400 MHz, $CDCl_3$):δ 8.74 (broad, s, 1H, NH); 7.80~6.70 (m, 7H); 6.20 (s, 1H); 3.90 (s, 3H); 3.50~2.60 (m, 11H).

Example 27

Preparation of 3-{1-[2-(5-methoxy-1-benzofuran-3-yl)ethyl]-1,2,3,6-tetrahydro-4-pyridinyl}-7-ethyl-1H-indole ("Compound 27")

3-{1-[2-(5-methoxy-1-benzofuran-3-yl)ethyl]-1,2,3,6-tetrahydro-4-pyridinyl}-7-ethyl-1H-indole was prepared by generally following the procedure outlined in example 24, step 6, starting from 2-(5-methoxy-1-benzofuran-3-yl)ethyl iodide (301 mg, 1 mmol) and 3 (1,2,3,6-tetrahydro-4-pyridinyl)-7-ethyl-1H-indole (226 mg, 1 mmol). The product was purified by silica-gel column chromatography by eluting it with 80% ethyl acetate:hexane. Brown solid; Yield: 156 mg (39%); 401 (M+H); □¹HMNR (400 MHz, CDCl₃):δ 8.04 (broad s, 1H, NH); 7.77~7.75 (d, 7.9 HZ, 1H); 7.51~6.88 (m, 7H); 6.23~6.21 (s, 1H); 3.85 (s, 3H); 3.36~2.65 (m, 12H); 1.25~1.27 (t, J=7.0 Hz, 3H).

Example 28

Preparation of 3-{1-[2-(1-benzothiophene-3-yl)ethyl]-1,2,3,6-tetrahydro-4-pyridinyl}-1H-indole ("Compound 28")

Step 1: To a stirred suspension of LiAlH₄ (200 mg, excess) in THF at 0° C., ethyl(-1-benzothiophene-3-yl)acetate (1.1 g, 5 mmol) in THF (20 mL) was added slowly. After the addition, the reaction mixture was stirred at room temperature for 1 hr and quenched with saturated NH₄Cl solution. The product was extracted with chloroform and washed well with water. It was dried over anhydrous MgSO₄; filtered and concentrated. The product, 2-(1-benzothiophene-3-yl)ethanol, was obtained as white oil pure enough and taken to the next step without purification. Yield: 850 mg (95%); 179 (M+H).

Step 2: To a stirred solution of 2-(1-benzothiophene-3-yl)ethanol (890 mg, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. It was extracted with chloroform, washed well with 5% Na₂S₂O₃ solution and the organic layer was dried over anhydrous MgSO₄. It was filtered and concentrated. The residue was purified by silica-gel column chromatography by eluting it with 30% ethyl acetate:hexane. The product, namely 2-(1-benzothiophene-3-yl)ethyl iodide, was obtained as brown liquid. Yield: 1.2 g (85%); 285 (M+H).

A mixture of 2-(1-benzothiophene-3-yl)ethyl iodide (284 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous MgSO₄ and concentrated to dryness. The dark colored solid was purified by silica-gel column chromatography by eluting it with 70% ethyl acetae: hexane. 3-{1-[2-(1-benzothiophene-3-yl)ethyl]-1,2,3,6-tetrahydro-4-pyridinyl}-1H-indole was isolated as yellow solid. mp 195–198° C.; Yield: 180 mg (50%); 359 (M+H); ¹HNMR (400 MHz, CDCl₃):δ 8.12 (broad s, 1H, NH); 7.92~6.69 (m, 10H); 6.25~6.23 (s, 1H); 3.48~2.60 (m, 10H).

Example 29

Preparation of 3-{1-[2-(1-benzothiophene-3-yl)ethyl]-1,2,3,6-tetrahydro-4-pyridinyl}-1-(2-propenyl)-1H-indole ("Compound 29")

3-{1-[2-(1-benzothiophene-3-yl)ethyl]-1,2,3,6-tetrahydro-4-pyridinyl}-1H-indole (358 mg, 1 mmol) (obtained from example 29, step 2) in dry THF (50 ml) was slowly added to a stirred suspension of hexane and washed with 60% sodium hydride (44 mg) at 0° C. After the addition, the reaction mixture was stirred for 330 min and allyl bromide (183 mg, 1.5 mmol) was added. The reaction mixture was stirred for 4 hrs and quenched carefully with ice cold water. The reaction mixture was extracted with chloroform; washed well with water; dried over anhydrous MgSO₄; filtered and concentrated. The residue obtained was purified by silica-gel column chromatography by eluting it with 50% ethyl acetate:hexane. Yellow semi-solid. Yield: 195 mg (48%); 399 (M+H); ¹HNMR (400 MHz, CDCl₃): δ 7.99~7.87 (m, 3H); 7.42~6.99 (m, 6H); 6.22~6.21 (s, 1H); 5.22~5.21 (d, J=1.3 Hz, 2H); 5.20~5.19 (d, J=1.3 Hz, 2H); 4.71~4.65 (d, 1.6 Hz, 2H); 3.49~2.67 (m, 10H).

Example 30

Preparation of 3-{1-[2-(1-benzothiophene-3-yl)ethyl]-1,2,3,6-tetrahydro-4-pyridinyl}-1-methyl-1H-indole ("Compound 30")

3-{1-[2-(1-benzothiophene-3-yl)ethyl]-1,2,3,6-tetrahydro-4-pyridinyl}-1H-indole (358 mg, 1 mmol) (obtained from example 29, step 2) in dry THF (50 ml) was slowly added to a stirred suspension of hexane and washed with 60% sodium hydride (44 mg) at 0° C. After the addition, the reaction mixture was stirred for 30 min and methyl iodide (213 mg, 1.5 mmol) was added. The reaction mixture was stirred for 4 hrs and quenched carefully with ice cold water. The reaction mixture was extracted with chloroform; washed well with water; dried over anhydrous MgSO₄; filtered and concentrated. The residue obtained was purified by silica-gel column chromatography by eluting it with 50% ethyl acetate:hexane. Light green semi-solid. Yield: 98 mg (26%); 373 (M+H); ¹HNMR (400 MHz, CDCl₃): 8.08~7.82 (m, 3H); 7.40~6.90 (m, 7H); 6.21~6.19 (s, 1H); 3.80 (s, 3H); 3.48~2.60 (m, 10H).

Example 31

Preparation of 3-{1-[2-(5-chloro-1-benzothiophene-3-yl)ethyl]-1,2,3,6-tetrahydro-4-pyridinyl}-1H-indole ("Compound 31")

Step 1: To a stirred suspension of LiAlH₄ (200 mg, excess) in THF at 0° C., ethyl(5-chloro-1-benzothiophene-3-yl)acetate (1.27 g, 5 mmol) in THF (20 mL) was added slowly. After the addition, the reaction mixture was stirred at room temperature for 1 hr and quenched with saturated NH₄Cl solution. The product was extracted with chloroform and washed well with water. It was dried over anhydrous MgSO₄; filtered and concentrated. The product, 2-(5-chloro-1-benzothiophene-3-yl)ethanol, was obtained as white oil, was pure enough and taken to the next step without purification. Yield: 920 mg (86%); 213 (M+H).

Step 2: To a stirred solution of 2-(5-chloro-1-benzothiophene-3-yl)ethanol (1060 mg, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. It was extracted with chloroform, washed well with 5% Na₂S₂O₃ solution and the organic layer was dried over anhydrous MgSO₄. It was filtered and concentrated. The residue was purified by silica-gel column chromatography by eluting it with 30% ethyl acetate:hexane. The product, namely 2-(5-chloro-1-benzothiophene-3-yl)ethyl iodide, was obtained as brown liquid; Yield: 1.1 g (69%); 319 (M+H).

A mixture of 2-(5-chloro-1-benzothiophene-3-yl)ethyl iodide (318 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous $MgSO_4$ and concentrated to dryness. The dark colored solid was purified by silica-gel column chromatography by eluting it with 70% ethyl acetate:hexane. 3-{1-[2-(1-benzothiophene-3-yl)ethyl]-1,2,3,6-tetrahydro-4-pyridinyl}-1H-indole was isolated as yellow oil; Yield: 115 mg (29%); 393 (M+H); $^1$H-NMR: δ 8.10(1H, s, NH), 7.91(1H, d, J=8 Hz), 7.77(2H, m), 7.25(6H, m), 6.24(1H, s), 3,37(2H, d, J=3 Hz), 3.18(2H, t, J=7.7 Hz), 2.87(4H, m), 2.68(2H, s).

Example 32

Preparation of 3-{1-[2-(5-chloro-1-benzothiophene-3-yl)ethyl]-1,2,3,6-tetrahydro-4-pyridinyl}-1-(2-propenyl)-1H-indole ("Compound 32")

3-{1-[2-(5-chloro-1-benzothiophene-3-yl)ethyl]-1,2,3,6-tetrahydro-4-pyridinyl}-1H-indole (392 mg, 1 mmol) (obtained from example 32, step 2) in dry THF (50 ml) was slowly added to a stirred suspension of hexane and was washed with 60% sodium hydride (44 mg) at 0° C. After the addition, the reaction mixture was stirred for 30 min and allyl bromide (183 mg, 1.5 mmol) was added. The reaction mixture was stirred for 4 hrs and quenched carefully with ice cold water. The reaction mixture was extracted with chloroform; washed well with water; dried over anhydrous $MgSO_4$; filtered and concentrated. The residue obtained was purified by silica-gel column chromatography by eluting it with 50% ethyl acetate:hexane. Yellow semi-solid. Yield: 156 mg (36%); 432 (M+H); $^1$H NMR: δ 7.90(1H, s, NH), 7.78(3H,m), 7.26(6H, m), 6.21(1H, s), 5.99(1H, m), 5.13 (2H, m), 4.71(2H, m), 3.40(2H, s), 3.15(2H, m), 2.92(4H, m), 2.68(2H, s).

Example 33

Preparation of 3-{1-[2-(5-chloro-1-benzothiophene-3-yl)ethyl]-1,2,3,6-tetrahydro-4-pyridinyl}-1-methyl-1H-indole ("Compound 33")

3-{1-[2-(5-chloro-1-benzothiophene-3-yl)ethyl]-1,2,3,6-tetrahydro-4-pyridinyl}-1H-indole (392 mg, 1 mmol) (obtained from example 32, step 2) in dry THF (50 ml) was slowly added to a stirred suspension of hexane washed 60% sodium hydride (44 mg) at 0° C. After the addition, the reaction mixture was stirred for 30 min and methyl iodide (213 mg, 1.5 mmol) was added. The reaction mixture was stirred for 4 hrs and quenched carefully with ice cold water. The reaction mixture was extracted with chloroform; washed well with water; dried over anhydrous $MgSO_4$; filtered and concentrated. The residue obtained was purified by silica-gel column chromatography by eluting it with 50% ethyl acetate:hexane. Brown semi-solid. Yield: 150 mg (36%); 407 (M+H); $^1$H NMR: δ 7.91(1H, m), 7.78(3H,m), 7.26(6H, m), 6.21(1H, s), 3.77(3H,s), 3.40(2H, s), 3.15(2H, m), 2.92(4H, m), 2.68(2H, s).

Example 34

Preparation of 3-{1-(2-Naphtho[1,2-b]furan-3-yl-ethyl)-piperidin-4-yl]-1H-indole ("Compound 34")

Step 1: To a stirred solution of 1-hydroxy-naphthalene-2-carboxylic acid methyl ester (20.2 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous $MgSO_4$ and filtered. It was concentrated and taken to next step without any purification. White oil; Yield: 22.0 g (92%); 239 (M+H).

Step 2: The 1-methoxycarbonylmethoxy-naphthalene-2-carboxylic acid methyl ester obtained from the step 1, (13.7 g, 50 mmol) was dissolved in THF:MeOH (1:1) (300 ml) and 5N NaOH (100 ml) was added. The reaction mixture was refluxed for 24 hrs and cooled to room temperature. At the end it was concentrated to dryness and dissolved in water. The aqueous layer was acidified with con. HCl and the separated solid was filtered. It was washed well with water and dried. The product, 1-carboxymethoxy-naphthalene-2-carboxylic acid was taken to step with out any purification. White solid; Yield: 10.0 g (81%); 247 (M+H).

Step 3: The 1-carboxymethoxy-naphthalene-2-carboxylic acid compound obtained from step 2 (12.3 g, 50 mmol) was dissolved in acetic anhydride (100 ml) and anhydrous sodium acetate (10.0 g, excess) was added. The reaction mixture was heated to 150° C. for 4 hrs. During this time the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, naphtho[1,2-b]furan-3 (2H)-one, precipitated from the reaction mixture. It was filtered and washed well with water. It was dried at 40° C. and used for the next step without further purifications. Yield: 4.5 g (48%); 185 (M+H).

Step 4: A mixture of naphtho[1,2-b]furan-3 (2H)-one (1.85 g, 10 mmol) and (carboxymethylene)triphenylphosphorane (5.22 g, 15 mmol) was refluxed in toluene (100 ml) for 48 hrs. At the end, reaction mixture was concentrated and loaded over a silica-gel column. The column was eluted with hexane (500 ml) and later with 25% ethyl acetate. The product, naphtho[1,2-b]furan-3-yl-acetic acid ethyl ester was obtained as a white oil. Yield: 2.2 g (86%); 255 (M+H).

Step 5: To a stirred suspension of $LiAlH_4$ (200 mg, excess) in THF at 0° C., naphtho[1,2-b]furan-3-yl-acetic acid ethyl ester (1.27 g, 5 mmol) in THF (20 mL) was added slowly. After the addition, reaction mixture was stirred at room temperature for 1 hr and quenched with saturated $NH_4Cl$ solution. The product was extracted with chloroform and washed well with water. It was dried over anhydrous $MgSO_4$; filtered and concentrated. The product, 2-naphtho[1,2-b]furan-3-yl ethanol, was obtained as white oil, was pure enough and taken to the next step without purification. Yield: 900 mg (84%); 213 (M+H).

Step 6: To a stirred solution of 2-naphtho[1,2-b]furan-3-yl ethanol (1.06 g, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. It was extracted with chloroform, washed well with 5% $Na_2S_2O_3$ solution and the organic layer was dried over anhydrous MgSO$_4$. It was filtered and concentrated. The residue was purified by silica-gel column chromatography by eluting it with 30% ethyl acetate:hexane. The product, namely 3-(2-iodo-ethyl)-naphtho[1,2-b]furan, was obtained as brown liquid. Yield: 1.4 g (87%); 322 (M+H).

A mixture of 3-(2-iodo-ethyl)-naphtho[1,2-b]furan (321 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous MgSO$_4$ and concentrated to dryness. The dark colored solid was purified by silica-gel column chromatography by eluting it with 70% ethyl acetate:hexane. 3-{1-(2-naphtho[1,2-b]furan-3-yl-ethyl)-1,2,3,6-tetrahydro-4-pyridinyl}-1H-indole was isolated as yellow solid. Yield: 120 mg (30%); 393 (M+H).

Step 7: 3-{1-(2-naphtho[1,2-b]furan-3-yl-ethyl)-piperidin-4-yl]-1H-indole (197 mg, 0.5 mmol) obtained from step 6, was hydrogenated over 10% Pd/C in ethanol at 40 psi pressure. At the end, reaction mixture was filtered through a pad of celite and concentrated. The product obtained was purified by silica-gel column chromatography by eluting it with 70% ethyl acetate:hexane 3-{1-(2-naphtho[1,2-b]furan-3-yl-ethyl)-piperidin-4-yl]-1H-indole was isolated as yellow solid; Yield: 160 mg (81%); 395 (M+H); $^1$H NMR: δ 8.30 (1H, d, J=8 Hz), 7.99 (1H, s, NH), 7.94(1H, d, J=8 Hz), 7.67(4H, m), 7.58(1H, t, J=8 Hz), 7.48(1H, t, J=8 Hz), 7.38(1H, d, J=8 Hz), 7.20(1H, t, J=8 Hz), 7.13(1H, t, J=8 Hz), 7.0(1H, s), 3.21(2H, d, J=12 Hz), 3.04(1H, m), 2.90 (1H, m), 2.84(2H, m), 2.29(2H, m), 2.13(2H, d, J=12 Hz), 1.90(2H, m, J=12 Hz).

Example 35

Preparation of 3-{1-[2-(1-benzofuran-3-yl)propyl]-1,2,3,6-tetrahydro-4-pyridinyl}-1H-indole ("Compound 35")

Step 1: A mixture of benzofuran-3 (2H)-one (1.34 g, 10 mmol) and ethyl-2-(triphenylphosphoranylidene)propionate (5.436 g, 15 mmol) was refluxed in toluene (100 ml) for 48 hrs. At the end, the reaction mixture was concentrated and loaded over silica-gel column. The column was eluted with hexane (500 ml) and later with 25% ethyl acetate. The product, ethyl(-1-benzofuran-3-yl)propanoate was obtained as a white oil. Yield: 1.6 g (67%); 219 (M+H).

Step 2: To a stirred suspension of LiAlH$_4$ (200 mg, excess) in THF at 0° C., ethyl(-1-benzofuran-3-yl)propanoate (1.09 g, 5 mmol) in THF (20 mL) was added slowly. After the addition, the reaction mixture was stirred at room temperature for 1 hr and quenched with saturated NH$_4$Cl solution. The product was extracted with chloroform and washed well with water. It was dried over anhydrous MgSO$_4$; filtered and concentrated. The product, 2-(1-benzofuran-3-yl)-1-propanol, was obtained as white oil, was pure enough and taken to the next step without purification. Yield: 700 mg (79%); 177 (M+H).

Step 3: To a stirred solution of 2-(1-benzofuran-3-yl)-1-propanol (880 mg, 5 mmol) in anhydrous pyridine (20 ml), p-toluenesulfonyl chloride (1.14 g, 6.0 mmol) was added. The reaction mixture was kept at 0° C. for 48 hrs and quenched with ice cold water. The reaction mixture was extracted with chloroform, washed well with water and dried over anhydrous MgSO$_4$. It was filtered and concentrated. The crude product obtained was taken to next step without any purification.

A mixture of tosylate (331 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous MgSO$_4$ and concentrated to dryness. The dark colored solid was purified by silica-gel column chromatography by eluting it with 70% ethyl acetate:hexane. 3-{1-[2-(1-benzofuran-3-yl)propyl]-1,2,3,6-tetrahydro-4-pyridinyl}-1H-indole was isolated as yellow oil; Yield: 110 mg (30%); 357 (M+H); $^1$HNMR (400 MHz, CDCl$_3$): δ 8.16~8.11 (s, 1H, NH); 7.91~6.99 (m, 10H); 6.21~6.10 (s, 1H); 3.70~2.60, 9H); 1.46~1.44 (d, J=7.0 Hz, 3H).

Example 36

Preparation of 3-{1-[2-(1-benzofuran-3-yl)propyl]-1,2,3,6-tetrahydro-4-pyridinyl}-6-fluoro-1H-indole ("Compound 36")

3-{1-[2-(1-benzofuran-3-yl)propyl]-1,2,3,6-tetrahydro-4-pyridinyl}-6-fluoro-1H-indole was prepared by generally following the procedure outlined in example 35, step 3, starting from the tosylate (example 36, step 3) (331 mg, 1 mmol) and 3 (1,2,3,6-tetrahydro-4-pyridinyl)-6-fluoro-1H-indole (216 mg, 1 mmol). The product was purified by silica-gel column chromatography by eluting it with 80% ethyl acetate:hexane. Brown oil; Yield: 148 mg (39%); 375 (M+H); $^1$HNMR (400 MHz, CDCl$_3$): δ 8.03 (broad s, 1H, NH); 7.79~6.89 (m, 9H); 6.17~6.15 (s, 1H); 3.35~2.60 (m, 9H); 1.46~1.44 (d, J=7.0 Hz, 3H).

Example 37

Preparation of 3-{1-[2-(1-benzofuran-3-yl)propyl]-1,2,3,6-tetrahydro-4-pyridinyl}-6-fluoro-1H-indole ("Compound 37")

3-{1-[2-(1-benzofuran-3-yl)propyl]-1,2,3,6-tetrahydro-4-pyridinyl}-5-fluoro-1H-indole was prepared by generally following the procedure outlined in example 35, step 3, starting from the tosylate (example 36, step 3) (331 mg, 1 mmol) and 3 (1,2,3,6-tetrahydro-4-pyridinyl)-5-fluoro-1H-indole (216 mg, 1 mmol). The product was purified by silica-gel column chromatography by eluting it with 80% ethyl acetate:hexane. Brown oil; Yield: 160 mg (42%); 375 (M+H); $^1$HNMR (400 MHz, CDCl$_3$): δ8.56~8.46 (broad s, 1H, NH); 7.65~6.94 (m, 9H); 6.10~6.09 (s, 1H); 3.48~2.58 (m, 9H); 1.46~1.44 (d, 7.0 Hz, 3H).

Example 38

Preparation of 3-{1-[2-(7-methoxy-1-benzofuran-3-yl)propyl]-1,2,3,6-tetrahydro-4-pyridinyl}-1H-indole ("Compound 38")

Step 1: A mixture of 7-methoxy-benzofuran-3 (2H)-one (1.64 g, 10 mmol) and ethyl-2-(triphenylphosphoranylidene) propionate (5.436 g, 15 mmol) was refluxed in toluene (100 ml) for 48 hrs. At the end, the reaction mixture was concentrated and loaded over a silica-gel column. The column was eluted with hexane (500 ml) and later with 25% ethyl acetate. The product, ethyl(7-methoxy-1-benzofuran-3-yl) propanoate, was obtained as a white oil. Yield: 1.9 g (76%); 249 (M+H).

Step 2: To a stirred suspension of LiAlH$_4$ (200 mg, excess) in THF at 0° C., ethyl(7-methoxy-1-benzofuran-3-yl)propanoate (1.24 g, 5 mmol) in THF (20 mL) was added slowly. After the addition, the reaction mixture was stirred at room temperature for 1 hr and quenched with saturated NH$_4$Cl solution. The product was extracted with chloroform and washed well with water. It was dried over anhydrous MgSO$_4$; filtered and concentrated. The product, 2-(7-methoxy-1-benzofuran-3-yl)-1-propanol, was obtained as white oil, was pure enough and taken to the next step without purification. Yield: 900 mg (87%); 207 (M+H).

Step 3: To a stirred solution of 2-(7-methoxy-1-benzofuran-3-yl)-1-propanol (1.03 g, 5 mmol) in anhydrous pyridine (20 ml), p-toluenesulfonyl chloride (1.14 g, 6.0 mmol) was added. The reaction mixture was kept at 0° C. for 48 hrs and quenched with ice cold water. The reaction mixture was extracted with chloroform, washed well with water and dried over anhydrous MgSO$_4$. It was filtered and concentrated. The crude product obtained was taken to next step without any purification.

A mixture of tosylate (360 mg. 1 mmol) (obtained by the above mentioned process) and 3 (1,2,3,6-tetrahydro-4-pyridinyl)-1H-indole (198 mg, 1 mmol) was heated at 120° C. in DMSO in the presence of N,N-diisopropylethylamine (5 ml, excess) for 24 hrs. At the end, the reaction mixture was quenched with water and extracted with chloroform. The organic layer was washed with water and dried over anhydrous MgSO$_4$ and concentrated to dryness. The dark colored solid was purified by silica-gel column chromatography by eluting it with 70% ethyl acetate:hexane. 3-{1-[2-(7-methoxy-1-benzofuran-3-yl)propyl]-1,2,3,6-tetrahydro-4-pyridinyl}-1H-indole was isolated as yellow solid. mp 156° C.; Yield: 160 mg (41%); 387 (M+H); $^1$H NMR (DMSO): δ☐11.2 (bs, 1H), 7.8 9s, 1H), 7.3–6.8 (m, 8H), 6.1 (bs, 1H), 3.9 (s, 3H), 3.3–2.6 (m, 9H), 1.4 (d, 3H).

Example 39

Preparation of 3-{1-[2-(7-methoxy-1-benzofuran-3-yl)propyl]-1,2,3,6-tetrahydro-4-pyridinyl}-5-fluoro-1H-indole ("Compound 39")

3-{1-[2-(7-methoxy-1-benzofuran-3-yl)propyl]-1,2,3,6-tetrahydro-4-pyridinyl}-5-fluoro-1H-indole was prepared by generally following the procedure outlined in example 38, step 3, starting from the tosylate (example 39, step 3) (360 mg, 1 mmol) and 3 (1,2,3,6-tetrahydro-4-pyridinyl)-5-fluoro-1H-indole (216 mg, 1 mmol). The product was purified by silica-gel column chromatography by eluting it with 80% ethyl acetate:hexane. Brown solid; Yield: 120 mg (29%); 405 (M+H); ☐$^1$HNMR (400 MHz, CDCl$_3$): δ8.13 (broad, 1H, NH); 7.90~6.20 (m, 7H); 6.10 (s, 1H); 3.96 (s, 3H); 3.30~2.60(m, 10H); 1.20~1.21 (d, J=7.2 Hz, 3H).

Example 40

Preparation of 3-{1-[2-(7-methoxy-1-benzofuran-3-yl)propyl]-1,2,3,6-tetrahydro-4-pyridinyl}-6-fluoro-1H-indole ("Compound 40")

3-{1-[2-(7-methoxy-1-benzofuran-3-yl)propyl]-1,2,3,6-tetrahydro-4-pyridinyl}-6-fluoro-1H-indole was prepared by generally following the procedure outlined in example 38, step 3, starting from the tosylate (example 39, step 3) (360 mg, 1 mmol) and 3 (1,2,3,6-tetrahydro-4-pyridinyl)-6-fluoro-1H-indole (216 mg, 1 mmol). The product was purified by silica-gel column chromatography by eluting it with 80% ethyl acetate:hexane. Brown solid; Yield: 180 mg (44%); 405 (M+H); $^1$HNMR (400 MHZ, CDCl$_3$):δ 8.13 (broad, s, 1H, NH); 7.90~6.30 (m, 7H), 6.10 (s, 1H); 3.96 (s, 3H); 3.30~2.60 (m, 10H); 120~1.23 (d, J=7.2 Hz, 3H).

Example 41

Preparation of 3-{1-[2-(7-methoxy-1-benzofuran-3-yl)-1-methylethyl]-1,2,3,6-tetrahydro-4-pyridinyl}-1H-indole ("Compound 41")

Step 1: A mixture of 7-methoxy-benzofuran-3 (2H)-one (1.64 g, 10 mmol) and 1-triphenylphosphoranylidene-2-propanone (4.77 g, 15 mmol) was refluxed in toluene (100 ml) for 48 hrs. At the end, the reaction mixture was concentrated and loaded over a silica-gel column. The column was eluted with hexane (500 ml) and later with 25% ethyl acetate. The product, 1-(7-methoxy-1-benzofuran-3-yl)acetone, was obtained as a red oil. Yield: 1.4 g (68%); 205 (M+H).

Step 2: To a stirred mixture of 1-(7-methoxy-1-benzofuran-3-yl)acetone (204 mg, 1 mmol) and 3 (1,2,3,6-tetrahydro-4-pyridinyl)-1H-indole (198.0 mg, 1 mmol) in 1,2-dichloroethane (100 ml) and acetic acid (1 ml), sodium triacetoxyborohydride (422 mg, 2 mmol) was added at room temperature. The reaction mixture was stirred at room temperature for 72 hrs. At the end, the reaction mixture was neutralized with 10% NaHCO$_3$ and extracted with chloroform. The organic layer was dried over anhydrous MgSO$_4$; filtered and concentrated. The product obtained was purified by silica-gel column chromatography by eluting it with 80% ethyl acetate:hexane. Brown solid; Yield: 150 mg (38%); 387 (M+H); $^1$HNMR (400 MHz, CDCl$_3$): δ☐8.31 (broad, s, 1H, NH); 7.92~6.88 (m, 8H); 6.25 (s, 1H); 3.85 (s, 3H); 3.50~2.60 (m, 10H); 1.03~1.05 (d, J=8.0 Hz, 3H).

Example 42

Preparation of 3-{1-[2-(7-methoxy-1-benzofuran-3-yl)-1-methylethyl]-1,2,3,6-tetrahydro-4-pyridinyl}-6-fluoro-1H-indole ("Compound 42")

3-{1-[2-(7-methoxy-1-benzofuran-3-yl)-1-methylethyl]-1,2,3,6-tetrahydro-4-pyridinyl}-6-fluoro-1H-indole was prepared by generally following the procedure outlined in example 41, step 2, starting from the 1-(7-methoxy-1-benzofuran-3-yl)acetone (204 mg, 1 mmol) and 3 (1,2,3,6-tetrahydro-4-pyridinyl)-6-fluoro-1H-indole (216.0 mg, 1 mmol) in 1,2-dichloroethane (100 ml) and acetic acid (1 ml), sodium triacetoxyborohydride (422 mg, 2 mmol). The product was purified by silica-gel column chromatography by eluting it with 80% ethyl acetate:hexane. Brown solid; Yield: 60 mg (14%); 405 (M+H); $^1$HNMR (400 MHz, CDCl$_3$): δ 8.31 (broad, s, 1H, NH); 7.92~6.88 (m, 7H); 6.25 (s, 1H); 3.85 (s, 3H); 3.50~2.60 (m, 10H); 1.03~1.05 (d, J=8.0 Hz, 3H).

Example 43

Preparation of 3-{1-[2-(5-methoxy-1-benzofuran-3-yl)-1-methylethyl]-1,2,3,6-tetrahydro-4-pyridinyl}-1H-indole ("Compound 43")

Step 1: A mixture of 5-methoxy-benzofuran-3 (2H)-one (1.64 g, 10 mmol) and 1-triphenylphosphoranylidene-2- propanone (4.77 g, 15 mmol) was refluxed in toluene (100 ml) for 48 hrs. At the end, reaction mixture was concentrated and loaded over silica-gel column. The column was eluted with hexane (500 ml) and later with 25% ethyl acetate. The product, 1-(5-methoxy-1-benzofuran-3-yl)acetone was obtained as a red oil. Yield: 1.1 g (53%); 205 (M+H).

Step 2: To a stirred mixture of 1-(5-methoxy-1-benzofuran-3-yl)acetone (204 mg, 1 mmol) and 3 (1,2,3,6-tetrahydro-4-pyridinyl)-1H-indole (198.0 mg, 1 mmol) in 1,2-dichloroethane (100 ml) and acetic acid (1 ml), sodium triacetoxyborohydride (422 mg, 2 mmol) was added at room temperature. The reaction mixture was stirred at room temperature for 72 hrs. At the end, the reaction mixture was neutralized with 10% $NaHCO_3$ and extracted with chloroform. The organic layer was dried over anhydrous $MgSO_4$; filtered and concentrated. The product obtained was purified by silica-gel column chromatography by eluting it with 80% ethyl acetate:hexane. Brown solid; Yield: 120 mg (31%); 387 (M+H); $^1$HNMR(400 MHz, $CDCl_3$):δ 8.31 (broad, s, 1H, NH); 7.92~6.88 (m, 8H); 6.25 (s, 1H); 3.85 (s, 3H); 3.50~2.60 (m, 10H); 1.03~1.05 (d, J=8.0 Hz, 3H).

Example 44

Preparation of 3-{1-[2-(5-chloro-1-benzofuran-3-yl)ethyl]-1,2,3,6-tetrahydropyridin-4-yl}imidazo[1,2-a]pyridine ("Compound 44")

Step 1: To a stirred solution of imidazo[1,2-a]pyridine (5.9 g, 50 mmol) in dry diethyl ether (100 ml) at room temperature, phenyllithium (1.8 M solution in cyclohexane:ether, 27.7 ml, 50 mmol) was slowly added. The reaction mixture was stirred at room temperature for 1 hr and cooled to −78° C. and tert-butyl-4-oxo-1-piperidine carboxylate (9.9 g, 50 mml) in THF (50 ml) was added slowly. Reaction mixture was stirred at room temperature for 4 hrs and quenched with ice cold water and extracted with chloroform; washed well with water and dried over anhydrous $MgSO_4$, filtered and concentrated. The product, 4-hydroxy-4-imidazo[1,2-a]pyridin-3-yl-piperidine-1-carboxylic acid tert-butyl ester, was purified by silica-gel column chromatography by eluting it with ethyl acetate. Yield: 6 g (37%); Brown oil; 320 (M+H).

Step 2: To a stirred solution of 4-hydroxy-4-imidazo[1,2-a]pyridin-3-yl-piperidine-1-carboxylic acid tert-butyl ester (2.0 g 6.26 mmol) in $CH_2Cl_2$ (100 ml) trifluoro acetic acid (10 ml) was added at room temperature. The reaction mixture was stirred at room temperature for 24 hrs. At the end, the reaction mixture was basified with methanolic ammonia and concentrated to dryness. The residue was directly chromatographed over silica-gel column and eluted with methanol:10% methanolic ammonia. The product, 4-imidazo[1,2-a]pyridin-3-yl-piperidin-4-ol was obtained as yellow oil; Yield; 620 mg (48%); 218 (M+H).

Step 3: To a stirred solution of methyl-5-chloro-2-hydroxy-benzoate (18.6 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous $MgSO_4$ and filtered. It was concentrated and taken to next step without any purification. White oil; Yield: 20.0 g (73%); 273 (M+H).

Step 4: The methyl-2-(ethoxy-2-oxoethoxy)-5-chloro-benzoate obtained from step 3, (13.6 g, 50 mmol) was dissolved in THF:MeOH (1:1) (300 ml) and 5N NaOH (100 ml) was added. The reaction mixture was refluxed for 24 hrs and cooled to room temperature. At the end it was concentrated to dryness and dissolved in water. The aqueous layer was acidified with con. HCl and the separated solid were filtered. It was washed well with water and dried. The product was taken to step without any purification. White solid; Yield: 8.0 g (69%); 231 (M+H).

Step 5: The 2-(carboxymethoxy)-5-chloro-benzoic acid compound obtained from step 4 (11.5 g, 50 mmol) was dissolved in acetic anhydride (100 ml) and anhydrous sodium acetate (10.0 g, excess) was added. The reaction mixture was heated to 150° C. for 4 hrs. During this time the reaction mixture turned dark red. The reaction mixture was cooled to room temperature and quenched carefully with ice cold water. The red solid obtained was filtered and washed well with water. The red solid obtained was suspended in 1 N hydrochloric acid and refluxed for 2 hrs. A dark red solid, 5-chloro-benzofuran-3 (2H)-one, precipitated from the reaction mixture. It was filtered and washed well with water. It was dried at 40° C. and used for the next step without further purifications. Yield: 3.8 g (45%); 169 (M+H).

Step 6: A mixture of 5-chloro-benzofuran-3 (2H)-one (1.68 g, 10 mmol) and (carboxymethylene)triphenylphosphorane (5.22 g, 15 mmol) was refluxed in toluene (100 ml) for 48 hrs. At the end, reaction mixture was concentrated and loaded over silica-gel column. The column was eluted with hexane (500 ml) and later with 25% ethyl acetate. The product, ethyl(5-chloro-1-benzofuran-3-yl)acetate was obtained as a white oil. Yield: 1.8 g (75%); 239 (M+H).

Step 7: To a stirred suspension of $LiAlH_4$ (200 mg, excess) in THF at 0° C., ethyl(5-chloro-1-benzofuran-3-yl)acetate (1.19 g, 50 mmol) in THF (20 mL) was added slowly. After the addition, reaction mixture was stirred at room temperature for 1 hr and quenched with saturated $NH_4Cl$ solution. The product was extracted with chloroform and washed well with water. It was dried over anhydrous $MgSO_4$; filtered and concentrated. The product 2-(5-chloro-1-benzofuran-3-yl)ethanol, was obtained as white oil, was pure enough and taken to the next step without purification. Yield: 850 mg (86%); 197 (M+H).

Step 8: To a stirred solution of 2-(5-chloro-1-benzofuran-3-yl)ethanol (980 mg, 5 mmol) in anhydrous pyridine (20 ml), p-toluenesulfonyl chloride (1.14 g, 6.0 mmol) was added. The reaction mixture was kept at 0° C. for 48 hrs and quenched with ice cold water. The reaction mixture was extracted with chloroform, washed well with water and dried over anhydrous $MgSO_4$. It was filtered and concentrated. The crude product obtained was taken to next step without any purification.

A mixture of tosylate (350 mg. 1 mmol) (obtained by the above mentioned process) and 4-imidazo[1,2-a]pyridine-3-yl-piperidin-4-ol (217 mg, 1 mmol) (obtained from step 2) was heated at 120° C. in DMSO in the presence of N,N-diisopropylethylamine (5 ml, excess) for 72 hrs. At the end, the reaction mixture was quenched with water and extracted with chloroform. The organic layer was washed with water and dried over anhydrous $MgSO_4$ and concentrated to dryness. The dark colored solid was purified by silica-gel column chromatography by eluting it with 100% ethyl acetate. 3-{1-[2-(5-chloro-1-benzofuran-3-yl)ethyl]-1,2,3,6-tetrahydro-4-pyridinyl}imidazo[1,2-a]pyridine was isolated as yellow oil. Yield: 110 mg (29%); 378 (M+H);

$^1$HNMR (400 MHz, $CDCl_3$): 8.46~8.28 (m, 1H); 7.94~6.03 (m, 8H); 6.02 (s, 1H); 3.41~2.58 (m, 10H).

Example 45

Testing of Compounds

The 5-HT transporter affinity of the compounds of this invention was established in accordance with standard pharmaceutically accepted test procedures with representative compounds as follows:

Rat Brain $^3$H-Paroxetine Binding Assay (RB 5HT Transporter)

This assay was used to determine a compound's affinity of the 5-HT transporter. A protocol similar to that used by Cheetham et. al. (*Neuropharmacol.*, 1993, 32: 737) was used. Briefly, frontal cortical membranes prepared from male S.D. rats were incubated with $^3$H-parxetine (0.1 nM) for 60 min. at 25° C. All tubes also contained either vehicle, test compound (one to eight concentrations), or a saturating concentration of fluoxetine (10 μM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine IC$_{50}$ values which were converted to K$_i$ values using the method of Cheng and Prusoff(*Biochem. Pharmacol.*, 1973, 22: 3099).

$$K_i = \frac{IC_{50}}{\text{Radioligand concentration}/(1 + KD)}$$

Inhibition of $^3$H-5-HT Uptake by Cells Possessing the Human 5-HT Transporter (HC 5HT Transporter)

A human carcinoma cell line (Jar cells) possessing low endogenous levels of the 5-HT-transporter are seeded into 96 well plates and treated with staurosporine at least 18 hrs prior to assay. [Staurosporine greatly increases the expression of the 5-HT-transporter.] On the day of assay, vehicle, excess of fluoxetine, or test compound is added to various wells on the plate. All wells then receive $^3$H-5-HT and are incubated at 37° C. for 5 min. The wells are then washed with ice cold 50 mM Tris HCl (pH 7.4) buffer and aspirated to remove free $^3$H-5-HT. 25 μl of 0.25 M NaOH is then added to each well to lyse the cells and 75 μl scintillation cocktail (Microscint™ 20) added prior to quantitation on a Packard TopCount machine. Tubes with vehicle represent total possible uptake, radioactivity counted in tubes with fluoxetine represent nonspecific binding/uptake and is subtracted from the total possible uptake to give total possible specific uptake. This nonspecific binding (usual low in number) is then subtracted from the counts obtained in wells with various test compounds (or different concentrations of test drug) to give specific uptake in the presence of drug. Specific uptake is then expressed as a % of control values and is analyzed using nonlinear regression analysis (Prizm) to determine IC$_{50}$ values. If the compound is active at inhibiting 5-HT uptake, its counts will be close to that obtained with fluoxetine.

High affinity for the serotonin 5-HT$_{1A}$ receptor was established by testing the claimed compound's ability to displace [$^3$H] 8-OH-DPAT (dipropylaminotetralin) from the 5-HT$_{1A}$ serotonin receptor following a modification of the procedure of Hall et al. (*J. Neurochem.*, 1985, 44: 1685) which utilizes CHO cells stably transfected with human 5-HT$_{1A}$ receptors. The 5-HT$_{1A}$ affinities for the compounds of the invention are reported below as K$_i$s.

Antagonist activity at 5-HT$_{1A}$ receptors was established by using a $^{35}$S-GTPγS binding assay similar to that used by Lazareno and Birdsall (*Br. J. Pharmacol.*, 1993, 109: 1120), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OH-DPAT. The test compound's maximum inhibitory effect is represented as the I$_{max}$, while its potency is defined by the IC$_{50}$.

Results from these two assays are presented below in Table I.

TABLE I

| Example | 5-HT$_{1A}$ K$_i$(nM) | RB-5HT Transporter K$_i$(nM) | HC-5HT Transporter K$_i$(nM) |
|---|---|---|---|
| Compound 1 | 36.11 | 1.33 | 210.00 |
| Compound 2 | 18.34 | 6.00 | Not tested |
| Compound 3 | Not tested | 156.00 | 328.00 |
| Compound 4 | 563.35 | 2.55 | 48.1 |
| Compound 5 | 42%* | 90.00 | 15.40 |
| Compound 6 | 248.05 | 14.00 | 282.00 |
| Compound 7 | 49%* | 12.00 | 126.00 |
| Compound 8 | 30%* | 300.00 | 600.00 |
| Compound 9 | 45%* | 3.54 | 54.20 |
| Compound 10 | 56.33 | 3.36 | 44.60 |
| Compound 11 | 66.35 | 3.63 | 66.80 |
| Compound 12 | 302.70 | 1.20 | 36.30 |
| Compound 13 | 12.67 | 3.36 | 34.10 |
| Compound 14 | 29%* | 14.00 | 59.70 |
| Compound 15 | 46%* | 15.00 | 152.00 |
| Compound 16 | 60%* | 3.00 | 49.10 |
| Compound 17 | 190.45 | 3.14 | 49.30 |
| Compound 18 | 41.47 | 4.13 | 25.30 |
| Compound 19 | 300.35 | 9.25 | 245.50 |
| Compound 20 | 8.46 | 2.85 | 190.00 |
| Compound 21 | 10.99 | 0.76 | 20.60 |
| Compound 22 | 10.09 | 3.17 | 493.00 |
| Compound 23 | 5.14 | 3.24 | 44.40 |
| Compound 24 | 23%* | 11.00 | 28.90 |
| Compound 25 | 44%* | 54.00 | 216.00 |
| Compound 26 | 8%* | 5.50 | 24.60 |
| Compound 27 | 39%* | 41.00 | 251.00 |
| Compound 28 | 67.90 | 6.25 | 11.05 |
| Compound 29 | 243.30 | 104.00 | 1120.00 |
| Compound 30 | 53.15 | 13.00 | 421.00 |
| Compound 31 | 29%* | 172.00 | 2900.00 |
| Compound 32 | 34%* | 132.00 | NT |
| Compound 33 | 45%* | 39.00 | NT |
| Compound 34 | 48%* | 62.00 | 276.00 |
| Compound 35 | 28%* | 16.00 | 130.00 |
| Compound 36 | 11%* | 4.43 | 42.00 |
| Compound 37 | 20%* | 21.00 | 152.00 |
| Compound 38 | 29.17 | 3.98 | 62.80 |
| Compound 39 | 48%* | 13.00 | 178.00 |
| Compound 40 | 48%* | 1.97 | 37.60 |
| Compound 41 | 11.48 | 8.93 | 68.80 |
| Compound 42 | 69.39 | 3.74 | 48.70 |
| Compound 43 | 34%* | 12.00 | 144.00 |
| Compound 44 | 44%* | 97.00 | 63.80 |

*% inhibition at 1 μM.

Hence, the compounds of this invention not only inhibit or block serotonin reuptake (thereby increasing levels of serotonin in the synapse) but also antagonize the 5-HT$_{1A}$ receptors (thereby reducing the latency period). The compounds of the invention would thus be useful in the prevention and/or treatment of diseases affected by disorders of the serotonin affected neurological systems, including depression, anxiety, cognitive deficits, such as those resulting from Alzheimer's disease and other neurodegenerative disorders, schizophrenia, prostate cancer, and nicotine withdrawal, by administration orally, parenterally, or by aspiration to a patient in need thereof.

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are herby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. The compound of formula I:

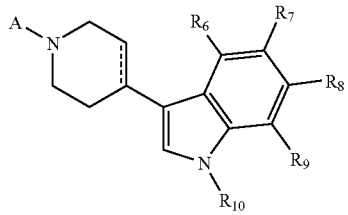

or an N-oxide, stereoisomer or pharmaceutically acceptable salt thereof;
wherein:
A is a heterocycle having the formula:

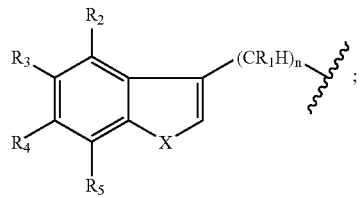

X is O;

$R_1$ is hydrogen, alkyl, cycloalkyl, alkenyl, alkynyl, fluoro, alkoxy, cycloalkoxy, hydroxy, nitrile, carboxy, alkoxycarbonyl, alkylcarbonyl, aminocarbonyl, alkylaminocarbonyl, fluorinated alkyl, aryl, aryloxy, alkylaryl, $NH_2$, $NHR_{11}$, $NR_{11}R_{11}$, —O-alkyl-$NR_{11}R_{11}$, or -aryl-O-alkyl-$NR_{11}R_{11}$;

$R_2$, $R_3$, $R_4$, $R_5$, $R_6$, $R_7$, $R_8$ and $R_9$ are, independently, hydrogen, alkyl, cycloalkyl, alkenyl, alkynyl, halo, cyano, alkoxy, cycloalkoxy, hydroxy, nitro, nitrile, $NH_2$, $NHR_{11}$, $NR_{11}R_{11}$, CHO, alkylcarbonyl, arylcarbonyl, carboxy, alkoxycarbonyl, alkoxycarbonylalkyl, alkylcarbonyloxy aminocarbonyl, alkylaminocarbonyl, fluorinated alkyl, aryl, aryloxy, alkylaryl, —O-alkyl-$NR_{11}R_{11}$, or -aryl-O-alkyl-$NR_{11}R_{11}$;

$R_{10}$ is hydrogen, alkyl, cycloalkyl, alkenyl of 3 to 6 carbon atoms (with the proviso that the carbon bearing the double bond should not be directly connected to N), alkynyl of 3 to 6 carbon atoms (with the proviso that the carbon bearing the triple bond should not be directly connected to N), alkoxycarbonyl, alkylcarbonyl, aminocarbonyl, alkylaminocarbonyl, fluorinated alkyl, aryl, alkylaryl, $SO_2$-aryl, or $SO_2$-alkyl;

$R_2$ and $R_3$, $R_3$ and $R_4$, or $R_4$ and $R_5$ can be attached together to form a cycloalkyl;

$R_{11}$ is hydrogen, optionally substituted with $R_2$, alkenyl, optionally substituted with $R_2$ (with the proviso that the carbon bearing the double bond is not bonded directly to the heteroatoms such as O, S or N—$R_{11}$), alkynyl optionally substituted $R_2$ (with the proviso that the carbon bearing the triple bond is not bonded directly to the heteroatoms such as O, S or N—$R_{11}$), aryl optionally substituted with $R_2$, alkylaryl optionally substituted with $R_2$, $SO_2$-aryl, or $SO_2$-alkyl;

with the proviso that if two $R_{11}$ groups are attached to nitrogen, then they can together form a 4 to 7 membered cyclic system having 0 to 2 hetero atoms selected from O, S=(O)$_r$, r is an integer from 0 to 2, and $NR_{11}$; and n is an integer from 1 to 6.

2. A compound according to claim 1, wherein said $R_1$ is hydrogen or alkyl.

3. A compound according to claim 1, wherein $R_2$, $R_3$, $R_4$, $R_5$, $R_6$, $R_7$, $R_8$, and $R_9$ are independently hydrogen, halo, alkyl, alkoxy, alkenyl, $NR_{11}R_{11}$, or cyano.

4. A compound according to claim 1, wherein said $R_{10}$ is hydrogen, alkyl, or aryl.

5. A compound according to claim 1, wherein said $R_{11}$ is hydrogen, alkyl, or aryl.

6. A compound according to claim 1, wherein said compound is:
    3-{1-[2-(1-benzofuran-3-yl)ethyl]-1,2,3,6-tetrahydro-4-pyridinyl}-1H-indole;
    3-{1-[2-(1-benzofuran-3-yl)ethyl]-1,2,3,6-tetrahydro-4-pyridinyl}-1-methyl-1H-indole;
    3-{1-[2-(1-benzofuran-3-yl)ethyl]-1,2,3,6-tetrahydro-4-pyridinyl}-7-ethyl-1H-indole;
    3-{1-[2-(1-benzofuran-3-yl)ethyl]-1,2,3,6-tetrahydro-4-pyridinyl}-6-fluoro-1H-indole;
    3-{1-[2-(1-benzofuran-3-yl)ethyl]-1,2,3,6-tetrahydro-4-pyridinyl}-5-cyano-1H-indole;
    3-{1-[2-(1-benzofuran-3-yl)ethyl]-1,2,3,6-tetrahydro-4-pyridinyl}-5-fluoro-1H-indole;
    3-{1-[2-(6-chloro-1-benzofuran-3-yl)ethyl]-1,2,3,6-tetrahydro-4-pyridinyl}-1H-indole;
    3-{1-[2-(6-chloro-1-benzofuran-3-yl)ethyl]-1,2,3,6-tetrahydro-4-pyridinyl}-5-fluoro-1H-indole;
    3-{1-[2-(6-chloro-1-benzofuran-3-yl)ethyl]-1,2,3,6-tetrahydro-4-pyridinyl}-6-fluoro-1H-indole;
    3-{1-[2-(6-methoxy-1-benzofuran-3-yl)ethyl]-1,2,3,6-tetrahydro-4-pyridinyl}-1H-indole;
    3-{1-[2-(6-methoxy-1-benzofuran-3-yl)ethyl]-1,2,3,6-tetrahydro-4-pyridinyl}-5-fluoro-1H-indole;
    3-{1-[2-(6-methoxy-1-benzofuran-3-yl)ethyl]-1,2,3,6-tetrahydro-4-pyridinyl}-6-fluoro-1H-indole;
    3-{1-[2-(6-methoxy-1-benzofuran-3-yl)ethyl]-1,2,3,6-tetrahydro-4-pyridinyl}-6-cyano-1H-indole;
    3-{1-[2-(5-chloro-1-benzofuran-3-yl)ethyl]-1,2,3,6-tetrahydro-4-pyridinyl}-1H-indole;
    3-{1-[2-(5-chloro-1-benzofuran-3-yl)ethyl]-1,2,3,6-tetrahydro-4-pyridinyl}-5-fluoro-1H-indole;
    3-{1-[2-(5-chloro-1-benzofuran-3-yl)ethyl]-1,2,3,6-tetrahydro-4-pyridinyl}-6-fluoro-1H-indole;
    3-{1-[2-(5-fluoro-1-benzofuran-3-yl)ethyl]-1,2,3,6-tetrahydro-4-pyridinyl}-1H-indole;
    3-{1-[2-(5-fluoro-1-benzofuran-3-yl)ethyl]-1,2,3,6-tetrahydro-4-pyridinyl}-5-cyano-1H-indole;

3-{1-[2-(5-fluoro-1-benzofuran-3-yl)ethyl]-1,2,3,6-tetrahydro-4-pyridinyl}-5-fluoro-1H-indole;
3-{1-[2-(7-methoxy-1-benzofuran-3-yl)ethyl]-1,2,3,6-tetrahydro-4-pyridinyl}-1H-indole;
3-{1-[2-(7-methoxy-1-benzofuran-3-yl)ethyl]-1,2,3,6-tetrahydro-4-pyridinyl}-6-fluoro-1H-indole;
3-{1-[2-(7-methoxy-1-benzofuran-3-yl)ethyl]-1,2,3,6-tetrahydro-4-pyridinyl}-5-fluoro-1H-indole;
3-{1-[2-(7-methoxy-1-benzofuran-3-yl)ethyl]-1,2,3,6-tetrahydro-4-pyridinyl}-5-cyano-1H-indole;
3-{1-[2-(5-methoxy-1-benzofuran-3-yl)ethyl]-1,2,3,6-tetrahydro-4-pyridinyl}-1H-indole;
3-{1-[2-(5-methoxy-1-benzofuran-3-yl)ethyl]-1,2,3,6-tetrahydro-4-pyridinyl}-5-fluoro-1H-indole;
3-{1-[2-(5-methoxy-1-benzofuran-3-yl)ethyl]-1,2,3,6-tetrahydro-4-pyridinyl}-6-fluoro-1H-indole;
3-{1-[2-(5-methoxy-1-benzofuran-3-yl)ethyl]-1,2,3,6-tetrahydro-4-pyridinyl}-7-ethyl-1H-indole;
3-{1-[2-(1-benzofuran-3-yl)propyl]-1,2,3,6-tetrahydro-4-pyridinyl}-1H-indole;
3-{1-[2-(1-benzofuran-3-yl)propyl]-1,2,3,6-tetrahydro-4-pyridinyl}-6-fluoro-1H-indole;
3-{1-[2-(1-benzofuran-3-yl)propyl]-1,2,3,6-tetrahydro-4-pyridinyl}-6-fluoro-1H-indole;
3-{1-[2-(7-methoxy-1-benzofuran-3-yl)propyl]-1,2,3,6-tetrahydro-4-pyridinyl}-1H-indole;
3-{1-[2-(7-methoxy-1-benzofuran-3-yl)propyl]-1,2,3,6-tetrahydro-4-pyridinyl}-5-fluoro-1H-indole;
3-{1-[2-(7-methoxy-1-benzofuran-3-yl)propyl]-1,2,3,6-tetrahydro-4-pyridinyl}-6-fluoro-1H-indole;
3-{1-[2-(7-methoxy-1-benzofuran-3-yl)-1-methylethyl]-1,2,3,6-tetrahydro-4-pyridinyl}-1H-indole;
3-{1-[2-(7-methoxy-1-benzofuran-3-yl)-1-methylethyl]-1,2,3,6-tetrahydro-4-pyridinyl}-6-fluoro-1H-indole;
3-{1-[2-(5-methoxy-1-benzofuran-3-yl)-1-methylethyl]-1,2,3,6-tetrahydro-4-pyridinyl}-1H-indole; or
3-{1-[2-(5-chloro-1-benzofuran-3-yl)ethyl]-1,2,3,6-tetrahydropyridin-4-yl}imidazo[1,2-a]pyridine.

7. A compound according to claim 1, wherein said compound is:
3-{1-[2-(1-benzofuran-3-yl)ethyl]-1,2,3,6-tetrahydro-4-pyridinyl}-1-methyl-1H-indole;
3-{1-[2-(1-benzofuran-3-yl)ethyl]-1,2,3,6-tetrahydro-4-pyridinyl}-5-cyano-1H-indole;
3-{1-[2-(6-chloro-1-benzofuran-3-yl)ethyl]-1,2,3,6-tetrahydro-4-pyridinyl}-6-fluoro-1H-indole;
3-{1-[2-(6-methoxy-1-benzofuran-3-yl)ethyl]-1,2,3,6-tetrahydro-4-pyridinyl}-1H-indole;
3-{1-[2-(6-methoxy-1-benzofuran-3-yl)ethyl]-1,2,3,6-tetrahydro-4-pyridinyl}-5-fluoro-1H-indole;
3-{1-[2-(6-methoxy-1-benzofuran-3-yl)ethyl]-1,2,3,6-tetrahydro-4-pyridinyl}-6-fluoro-1H-indole;
3-{1-[2-(6-methoxy-1-benzofuran-3-yl)ethyl]-1,2,3,6-tetrahydro-4-pyridinyl}-6-cyano-1H-indole;
3-{1-[2-(5-chloro-1-benzofuran-3-yl)ethyl]-1,2,3,6-tetrahydro-4-pyridinyl}-1H-indole;
3-{1-[2-(5-chloro-1-benzofuran-3-yl)ethyl]-1,2,3,6-tetrahydro-4-pyridinyl}-5-fluoro-1H-indole;
3-{1-[2-(5-chloro-1-benzofuran-3-yl)ethyl]-1,2,3,6-tetrahydro-4-pyridinyl}-6-fluoro-1H-indole;
3-{1-[2-(5-fluoro-1-benzofuran-3-yl)ethyl]-1,2,3,6-tetrahydro-4-pyridinyl}-1H-indole;
3-{1-[2-(5-fluoro-1-benzofuran-3-yl)ethyl]-1,2,3,6-tetrahydro-4-pyridinyl}-5-cyano-1H-indole;
3-{1-[2-(7-methoxy-1-benzofuran-3-yl)ethyl]-1,2,3,6-tetrahydro-4-pyridinyl}-6-fluoro-1H-indole;
3-{1-[2-(7-methoxy-1-benzofuran-3-yl)propyl]-1,2,3,6-tetrahydro-4-pyridinyl}-6-fluoro-1H-indole;
3-{1-[2-(7-methoxy-1-benzofuran-3-yl)-1-methylethyl]-1,2,3,6-tetrahydro-4-pyridinyl}-1H-indole; or
3-{1-[2-(7-methoxy-1-benzofuran-3-yl)-1-methylethyl]-1,2,3,6-tetrahydro-4-pyridinyl}-6-fluoro-1H-indole.

8. A composition, comprising the compound of claim 1 and one or more pharmaceutically acceptable carriers.

* * * * *